United States Patent
Felder-Flesch et al.

(10) Patent No.: US 9,623,127 B2
(45) Date of Patent: Apr. 18, 2017

(54) MULTIMODAL CONTRAST AND RADIOPHARMACEUTICAL AGENT FOR AN IMAGING AND A TARGETED THERAPY GUIDED BY IMAGING

(75) Inventors: Delphine Felder-Flesch, Hattstatt (FR); Claire Billotey, Lyons (FR); Giuseppe Lamanna, Strasbourg (FR); Marc Janier, Limas (FR); David Kriza, Lyons (FR)

(73) Assignees: CENTRE NATIONAL DE LA RECHERCHE SCIENTIFIQUE, Paris (FR); HOSPICES CIVILS DE LYON, Lyons (FR); UNIVERSITE DE STRASBOURG, Strasbourg (FR); UNIVERSITE CLAUDE BERNARD LYON 1, Villeurbanne (DE)

(*) Notice: Subject to any disclaimer, the term of this patent is extended or adjusted under 35 U.S.C. 154(b) by 228 days.

(21) Appl. No.: 14/358,818

(22) PCT Filed: Nov. 8, 2011

(86) PCT No.: PCT/IB2011/003109
§ 371 (c)(1),
(2), (4) Date: Jun. 25, 2014

(87) PCT Pub. No.: WO2013/072717
PCT Pub. Date: May 23, 2013

(65) Prior Publication Data
US 2014/0336368 A1    Nov. 13, 2014

(51) Int. Cl.
*A61K 51/04* (2006.01)
*A61K 49/18* (2006.01)
*C07B 59/00* (2006.01)
*A61K 49/00* (2006.01)
*A61K 49/12* (2006.01)

(52) U.S. Cl.
CPC ...... *A61K 51/0478* (2013.01); *A61K 49/1824* (2013.01); *C07B 59/004* (2013.01); *A61K 49/0021* (2013.01); *A61K 49/124* (2013.01); *Y10T 428/2982* (2015.01)

(58) Field of Classification Search
USPC .......................................................... 532/14
See application file for complete search history.

(56) References Cited

U.S. PATENT DOCUMENTS 8,404,216 B2    3/2013  Felder-Flesch et al.

FOREIGN PATENT DOCUMENTS

| FR | 2906806 A1 | 4/2008 |
|---|---|---|
| WO | 2008043911 A2 | 4/2008 |
| WO | 2011131912 A1 | 10/2011 |

OTHER PUBLICATIONS

Translation of WO2011/131912A1.*
Bertin et al., "Synthesis and characterization of a highly stable dendritic catechol-tripod bearing technetium-99m", New Journal of Chemistry, 2010, vol. 34, pp. 267-275.
International Search Report, dated Aug. 1, 2012, from corresponding PCT application.

* cited by examiner

*Primary Examiner* — Michael G Hartley
*Assistant Examiner* — Melissa Perreira
(74) *Attorney, Agent, or Firm* — Young & Thompson

(57) ABSTRACT

A multimodal contrast and radiopharmaceutical agent for an imaging and a targeted therapy guided by imaging.

12 Claims, 9 Drawing Sheets

MULTIMODAL CONTRAST AND RADIOPHARMACEUTICAL AGENT FOR AN IMAGING AND A TARGETED THERAPY GUIDED BY IMAGING

FIELD OF THE INVENTION

The present invention relates to a multimodal contrast and radiopharmaceutical agent for an imaging and a targeted therapy guided by imaging.

BACKGROUND OF THE INVENTION

The vectorization of diagnostic and especially therapeutic tools is a very important stake. Indeed, to bring, thanks to a "vehicle", therapeutic objects (medicines, physical agents) specifically at the level of the therapeutic targets (typically tumour cells) can allow increasing both the concentration and efficiency of these therapies, while decreasing their side-effects resulting from a nonspecific distribution. So, the use of a highly efficient but very toxic substance can be envisaged with a system of effective targeting. In bioimaging, targeting allows refining the diagnosis by improving the sensibility and especially the specificity for an earlier diagnosis. Qualitative and quantitative study of the internalization in the therapeutic target could previously be done by imaging with the same nanoprobe (organic molecule with a nanometric size in contrast to nanoparticles that are inorganic molecules with a nanometric size) allowing adapting the level of the therapeutically injected radioactivity.

But this objective, pursued by numerous teams in the field of therapy, meets important obstacles related in particular to the non optimal specificity of the vector for the target which ends in a too low ratio [therapeutic object in tissue to treat]/[therapeutic object in healthy tissue]. Such problem is connected to the fact that, except the central nervous system, there are no membrane, enzymatic or other structures which are specific of a single type of cell; in other words, there are no targets totally specific of a given cellular population, but simply an over-expression of these targets. Indeed, the tumor cells only differ from normal cells by an over-expression of cellular "markers". Thus, the targeting of specific cells by a single marker often comes along with a bad targeting specificity and then large side-effects.

Therefore, a dendritic approach to in vivo efficient targeting seems promising as it combines several advantages such as:
  increasing sharply the binding ratio of the nanoprobe on the target tissue by increasing the number of biological effectors within a same nanoprobe;
  allowing a multi-modal imaging (magnetic resonance imaging (MRI), positron emission tomography (PET), single photon emission computed tomography (SPECT)) through complexation of diverse metallic ions;
  having favorable biodistribution properties.

Indeed, elimination of the non targeted complexes is essential and can be done by several routes, in particular by renal route or hepatic and biliary way.

Moreover, the dendritic globular shape could improve the coupling stability with the biological effectors as well as the thermodynamic and kinetic stability of the metallic complex.

The use of dendrimers or dendritic compounds for biomedical applications is a flourishing area of research, mainly because of their precisely defined structure and high tunability, leading to biocompatible, polyfunctional and water-soluble systems (S. E. Stiriba, H. Frey and R. Haag, *Angew. Chem. Int. Ed.*, 2002, 41, 1329-1334; M. J. Cloninger, *Curr. Opin. Chem. Biol.*, 2002, 6, 742-748; R. Duncan and L. Izzo, *Adv. Drug Delivery Rev.*, 2005, 57, 2215-2237; C. C. Lee, J. A. MacKay, J. M. J. Fréchet and F. C. Szoka, *Nat. Biotechnol.*, 2005, 23, 1517-1526; O. Rolland, C-O. Turrin, A-M. Caminade, J-P. Majoral, *New J. Chem.*, 2009, 33, 1809-1824).

Dendritic Contrast Agents and Radiopharmaceuticals
a) Gadolinium-Based Contrast Agents In recent years, a number of research groups have explored the use of dendrimers as a new class of macromolecular (MRI) contrast agents. The efficiency of MRI contrast agents is often expressed in terms of their longitudinal relaxivity ($r_1/mM^{-1} \cdot s_{-1}$), i.e. their ability to shorten the longitudinal relaxation time of protons of water molecules ($T_1$/s).

In seminal work, Wiener et al. (E. C. Wiener, M. W. Brechbiel, H. Brothers, R. L. Magin, O. A. Gansow, D. A. Tomalia and P. C. Lauterbur, *Magn. Reson. Med.*, 1994, 31, 1) reported the synthesis of different generations of Gd(III) DTPA-based PAMAM dendrimers. Their sixth generation dendritic MRI contrast agent (MW=139 kg·mol-1) displayed an $r_1$ of 34 $mM^{-1} \cdot s^{-1}$ (0.6 T, 20° C.), which was six times higher than the $r_1$ of Gd(III)DTPA (MW=0.55 kg·mol-1, $r^1$=5.4 $mM^{-1} \cdot s^{-1}$). This strong increase in $r_1$ was ascribed to the lower molecular tumbling rate of the Gd(III)DTPA complex at the periphery of the dendrimer, as evidenced from the increase in the rotational correlation times (E. C. Wiener, F. P. Auteri, J. W. Chen, M. W. Brechbiel, O. A. Gansow, D. S. Schneider, R. L. Belford, R. B. Clarkson and P. C. Lauterbur, *J. Am. Chem. Soc.*, 1996, 118, 7774). Interestingly, no increase in $r_1$ value was observed for flexible macromolecular polymers of comparable molecular weight (V. S. Vexler, O. Clement, H. Schmitt-Willich and R. C. Brasch, *J. Magn. Reson. Imaging*, 1994, 4, 381; T. S. Desser, D. L. Rubin, H. H. Muller, F. Qing, S. Khodor, G. Zanazzi, S. W. Young, D. L. Ladd, J. A. Wellons and K. E. Kellar, *J. Magn. Reson. Imaging*, 1994, 4, 467) implying that segmental motion dominates the rotational correlation time. Bryant et al. investigated the relationship between $r_1$ and the molecular weight of the dendritic MRI contrast agent using different generations of Gd(III)DOTA-based PAMAM dendrimers (L. H. Bryant, Jr, M. W. Brechbiel, C. Wu, J. W. Butte, V. Herynek and J. A. Frank, *J. Magn. Reson. Imaging*, 1999, 9, 348). In that case, a plateau value for $r_1$ of 36 $mM^{-1} \cdot s^{-1}$ (0.47 T, 20° C.) was reached for the seventh generation of Gd(III)DOTA-based dendrimer (MW=375 kg·mol$^{-1}$). Moreover, it was demonstrated that $r_1$ of the seventh generation dendrimer increases with increasing temperature, indicating that slow water exchange limits the relaxivity (E. Toth, D. Pubanz, S. Vauthey, L. Helm and A. E. Merbach, *Chem. Eur. J.*, 1996, 2, 1607). Rudovsky et al. studied the effect on $r_1$ of the ionic interactions between negatively charged Gd(III)-based PAMAM dendrimers and positively-charged poly(aminoacids) (J. Rudovsky, P. Hermann, M. Botta, S. Aime and I. Lukes, *Chem. Commun.*, 2005, 2390). Titration experiments on the second generation dendritic contrast agent with poly(arginine) showed an increase in $r_1$ from 20 to 28 $mM^{-1} \cdot s^{-1}$ (0.47 T, 20° C.). This effect was attributed to a decrease in the mobility of the Gd(III) complex, induced by interactions between the anionic dendrimer and the cationic poly(arginine). A series of Gd(III)DTPA-functionalized PPI dendrimers was reported by Kobayashi et al. (H. Kobayashi, S. Kawamoto, S.-K. Jo, H. L. Bryant, Jr, M. W. Brechbiel, Jr and R. A. Star, *Bioconjugate Chem.*, 2003, 14, 388). The authors demonstrated that $r_1$ almost linearly increased with the molecular weight of the dendrimer without reaching a plateau value, eventually resulting in a $r_1$ value of 29 mM$^{-1} \cdot$s$^{-1}$ (1.5 T, 20° C.) for the fifth generation of dendritic contrast agent. Later on, E. W. Meijer et al. reported a novel series of Gd(III) DTPA-based PPI dendrimers utilizing a different linker between the Gd(III) complex and the dendrimer. (S. Langereis, Q. G. de Lussanet, M. H. P. van Genderen, W. H. Backes and E. W. Meijer, *Macromolecules*, 2004, 37, 3084) Also, for these dendrimers, a significant increase in $r_1$, though not as pronounced as for the dendritic MRI contrast agents reported by Kobayashi et al., was observed, while molecular weights of both systems were comparable (fifth generation: $r_1$=20 mM$^{-1} \cdot$s$^{-1}$, 1.5 T and 20° C.). Researchers at Schering AG (Berlin, Germany) have developed a lysine-based class of dendritic contrast agents: Gadomer-17® ($r_{1=15.2}$ mM$^{-1} \cdot$s$^{-1}$, 1.5 T and 37° C.). (C. Fink, F. Kiessling, M. Bock, M. P. Lichy, B. Misselwitz, P. Peschke, N. E. Fusenig, R. Grobholz and S. Delorme, *J. Magn. Reson. Imaging*, 2003, 18, 59; G. M. Nicolle, E. Toth, H. Schmitt-Willich, B. Raduchel and A. E. Merbach, *Chem. Eur. J.*, 2002, 8, 1040; G. Adam, J. Neuerburg, E. Spuntrup, A. Muhler, K. Scherer and R. W. Gunther, *J. Magn. Reson. Imaging*, 1994, 4, 462; G. Adam, J. Neuerburg, E. Spuntrup, A. Muhler, K. Scherer and R. W. Gunther, *Magn. Reson. Med.*, 1994, 32, 622; H. C. Schwickert, T. P. Roberts, A. Muhler, M. Stiskal, F. Demsar and R. C. Brasch, *Eur. J. Radiol.*, 1995, 20, 144; H. C. Roberts, M. Saeed, T. P. Roberts, A. Muhler, D. M. Shames, J. S. Mann, M. Stiskal, F. Demsar and R. C. Brasch, *J. Magn. Reson. Imaging*, 1997, 7, 331). These macromolecular MRI contrast agents were synthesized from a trimesoyltriamide central core, to which 18 lysine amino acid residues were introduced.

In all these examples, dendrimers have shown to be suitable synthetic scaffolds for the incorporation of multiple Gd(III) moieties, leading to an improved sensitivity for MRI in terms of $r_1$. These conclusions are based on measurements at current magnetic fields of 0.5-1.5 T. However, at high magnetic fields of 10 T, the $r_1$ values of dendritic contrast agents are substantially lower, not exceeding the $r_1$ values of low molecular weight Gd(III)-based complexes. Dendrimers also improve the protection of the gadolinium and its stability and thus decrease the toxicity risks.

The dendritic MRI contrast agents are excellent blood pool agents. However, these structures lack the specificity required for molecular MRI (D. Artemov, *J. Cell. Biochem.*, 2003, 90, 518). The development of target-specific MRI contrast agents, directed to defined molecular markers, could dramatically improve the targeting and imaging of a specific disease, due to the accumulation of MRI contrast agent at the region of interest.

b) Dendritic Radiopharmaceuticals

The use of dendrimers for the complexation of $^{99m}$Tc was scarcely reported in the literature so far: in 2001, F. Vögtle et al. (H. Stephan, H. Spies, B. Johannsen, K. Gloe, M. Gorka, F. Vögtle, *Eur. J. Inorg. Chem.*, 2001, 2957-2963) reported host-guest properties of multi-crown dendrimers of four different generations towards sodium pertechnetate. Extraction studies performed showed that the guest molecules are mainly bound in the interior of the polyamine squeleton. The same year, H. Mukhtar and coll. (M. Subbarayan, S. J. Shetty, T. S. Srivastava, O. P. D. Noronha, A. M. Samuel, H. Mukhtar, *Biochem. and Biophys. Res. Commun.*, 2001, 281, 32-36) reported the synthesis and in vivo distribution of water-soluble $^{99m}$Tc-labeled dendritic porphyrins for tumor imaging and diagnosis: these dendritic systems were administered to C6-glioma tumor bearing Wistar rats and scinti-imaging studies showed their potential for early stage tumor detection. Finally, A. Adronov, J. F. Valliant et al (M. C. Parrott, S. R. Benhabbour, C. Saab, J. A. Lemon, S. Parker, J. F. Valliant, A. Adronov, *J. Am. Chem. Soc.*, 2009, 131, 2906-2916) published very recently a paper dealing with the use of high-generation polyester dendrimers to complex 99mTc and their use for SPECT imaging: it was found that all three dendrimer generation (G5 to G7) were rapidly and efficiently removed from the bloodstream via the kidneys and excreted through the bladder within 15 min post injection. The SPECT-CT data were corroborated with a quantitative biodistribution study involving ex vivo harvesting of various organs and determining the radioactivity within the organs as a function of time.

The international application WO2008/043911, relates to chelated dendritic complexes and their applications biomedical imaging; such complexes have the following formula:

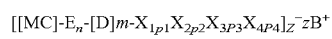

$$[[MC]\text{-}E_n\text{-}[D]m\text{-}X_{1p1}X_{2p2}X_{3p3}X_{4p4}]_z^-zB^+$$

wherein:

M is a magnetic cation, in particular chosen among Gd$^{3+}$, Mn$^{2+}$ and 99mTc$^{3+}$, C is a chelating agent of the magnetic marker M,

[MC] is a chelate of the magnetic marker M,

E is a spacer, n=0 or 1,

[D] is a dendritic structure having a core comprising at least one group derived from benzyl alcohol or a benzylamine, the benzyl cycle of which is substituted in positions 3, 4, 5 by dendrites composed of polyethyleneglycol pattern, m is an integer being equal to 1 or 2 or 4, Xi is a group increasing the complex lipophily, such as a tert-butyl group (tBu), p1 is an integer from 0 to 12, X2 is a group increasing the complex specificity for a particular organ, preferably for the brain, such as L-dopamine, p2 is an integer being equal to 0, 1, 2, or 4, X3 un group having a therapeutic activity, preferably for neurodegeneratives diseases such as Alzheimer disease, Parkinson disease and multiple sclerosis, p3 is an integer equal to 0, 1, 2, or 4, X4 is a CH3 group, p4 is an integer from 0 to 12 p1+p2+p3+p4=3 when m=1 or p1+p2+p3+p4=6 when m=2 or p1+p2+p3+p4=12 when m=4,

B counter ion, preferably Na$^+$ or K$^+$, z is an integer equal to 0, 1, 2, 3 or 4.

Nevertheless, the application WO2008/043911 is very confusing for a man skilled in the art because:

- on one hand preferred compounds are complexes of the formula defined above wherein dendrites of each structure [D] are functionalized with L-Dopamine but it is well known for a man skilled in the art that dopamine does not cross the blood brain barrier and further the specification discloses a dendrite [D] that is not functionalized with L-Dopamine but with a 3,4 OH phenylglycine.
- on the other hand, example 2 discloses the synthesis of compound of formula III-1 to 111-3 but said synthesis could not be achieved as the compound disclosed before the reaction with a metallic moiety could not lead at all said formulas.

Thus in view of this international application, a man skilled in the art does not know the exact functionalities to be introduced in the general formula to give an imaging agent with brain specificity.

An article published in New Journal of chemistry (2010), 34, 267-275, disclosed compounds having the following structures 1 and 2:
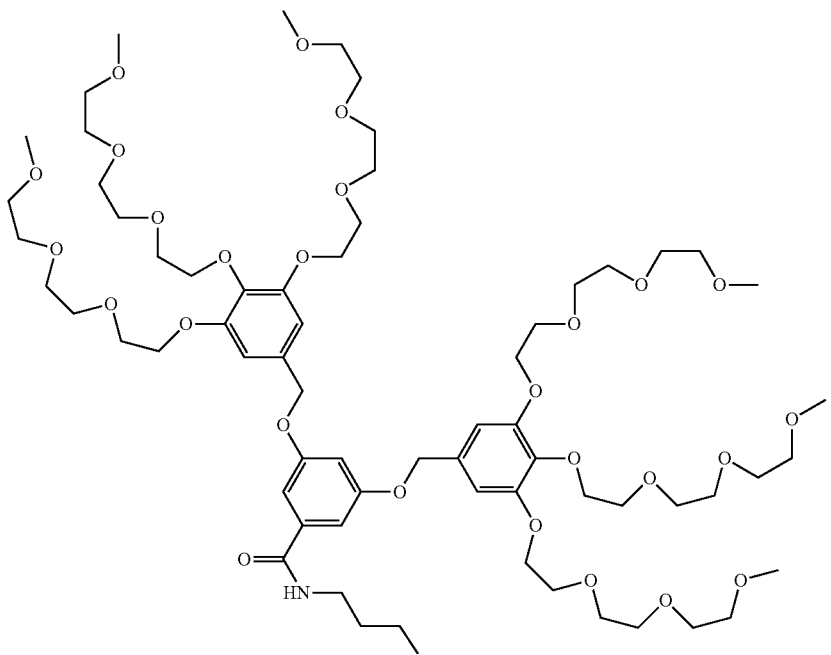
1
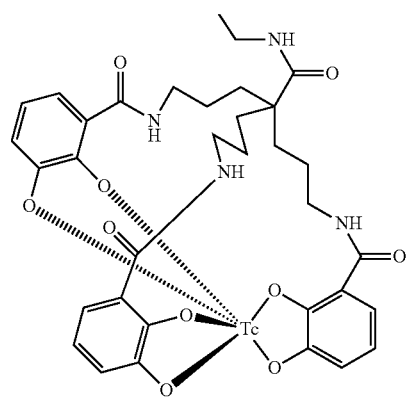

-continued

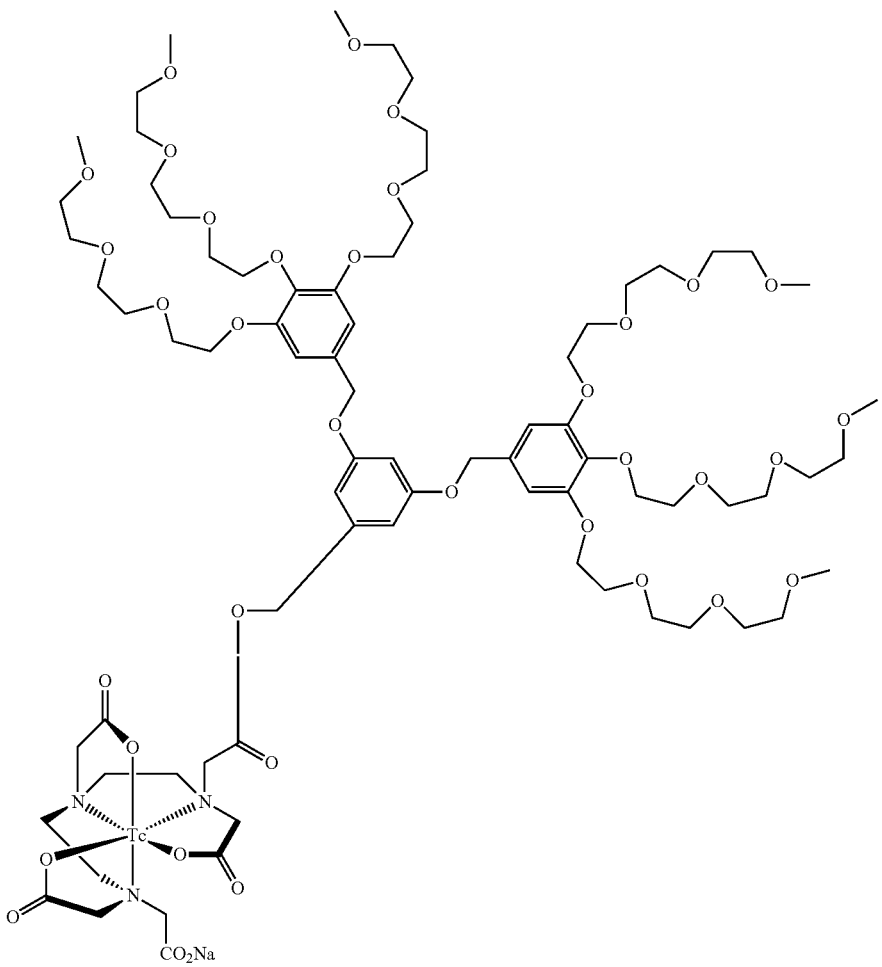

as imaging agents. No functionalization of the oligoethylene pattern group is described, but it is concluded that grafting L-Dopamine to the dendron periphery will allow the elaboration of brain-targeting radiopharmaceuticals.

Thus the teaching of this document is as confusing as the one of the international application WO2008/043911.

SUMMARY OF THE INVENTION

One of the aims of the present invention is to provide dendritic nanoprobes comprising several identical or different recognition elements of a target cell, in particular a cancer cell displaying important targeting capacities and allowing the vectorization of diagnostic or therapeutic agent through the complexation of very diverse metallic ions, said dendritic nanoprobes being liable to cross the blood brain bather.

Another aim of the invention is to provide dendritic nanoprobes as a medicament, suitable especially for detecting and/or treating a cancer cell or tissue or organ.

Still another aim of the invention is to provide pharmaceutical or diagnostic compositions comprising dendritic nanoprobes.

The present invention relates to functionalized dendritic nanoprobes of the following formula (I)

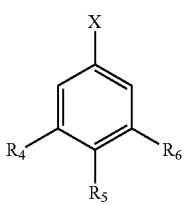

(I)

wherein:
for generation 1, $R_4$ and $R_6$ represent independently from each other a chain composed of oligoethyleneglycol patterns, at least one of said oligoethyleneglycol chain being functionalized at its extremity by a group chosen among a biological molecule, a fluorophore, or a biocompatible dye and $R_5$ represents an hydrogen atom or a chain composed of oligoethyleneglycol patterns, said chain being optionally functionalized at its extremity by a group chosen among a biological molecule, a fluorophore, or a biocompatible dye,
for higher generations, $R_5$ represents an hydrogen atom and $R_4$ and $R_6$ represent a dendritic structure (D)m comprising at least one ether of benzyl alcohol, said benzyl being substituted either at positions 3, 4, 5, or at positions 3 and 5 by chains composed of oligoethyleneglycol patterns, at least one of said oligoethyleneglycol chain being functionalized at its extremity by a group chosen among a biological molecule, a fluorophore, or a biocompatible dye and m=1, 2 or 4, X represents a group of the following formula (II):

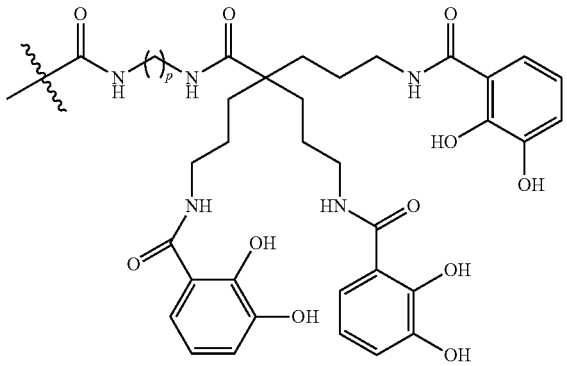

wherein:
p is comprised from 3 to 6,

DETAILED DESCRIPTION OF THE INVENTION

The word "functionalized" means that in the compounds of formula (I) at least one of R4 to R6 groups is functionalized by a biological molecule, a fluorophore or a dye.

The "oligoethyleneglycol pattern" refers to the following structure:
A for $R_4$ and $R_6$:
A

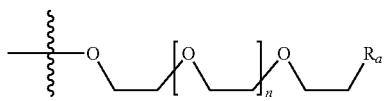

wherein n is an integer varying from 1 to 10,
B for $R_5$:

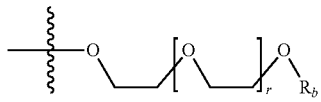

wherein r is an integer varying from 1 to 20,
$R_a$ and $R_b$ are independently from each other a linear or branched $(C_1-C_{10})$-alkyl group or a biological molecule, a fluorophore or a dye.

Alkyl group can be methyl, ethyl, propyl, butyl, pentyl, hexyl, heptyl, octyl, nonyl, decyl and isomers thereof.

In particular, alkyl group is methyl or tert-butyl.

By the expression "biological molecule" is meant a molecule liable to display a biological function, i.e. any molecule produced by a living organism, such as lipids, phospholipids, glycolipids, sterols, glycerolipids, vitamins, hormones, neurotransmitters, amino-acids, saccharides, nucleotides, antibodies, without being limited to them, or any chemically produced molecule such as a drug or an active principle.

The expression "fluorophore" refers to fluorescent molecules such as cyanins, alexa . . . well known from a man skilled in the art, in particular fluorophore used in FACS method, but without being limited to them.

The term "dye" refers to any natural dye liable to be used as a dye for food, pharmaceutical or cosmetical products, such as those disclosed in M. Perez-Urquiza et al (2001) *J. Chrom.* 917, 331-336. Preferably, the dye has a blue color to better identify cells or tissues. As an example, Patent Blue V, also called Food Blue 5 or Sulphan Blue, or patent blue Vf having respectively the following formulas, can be used:

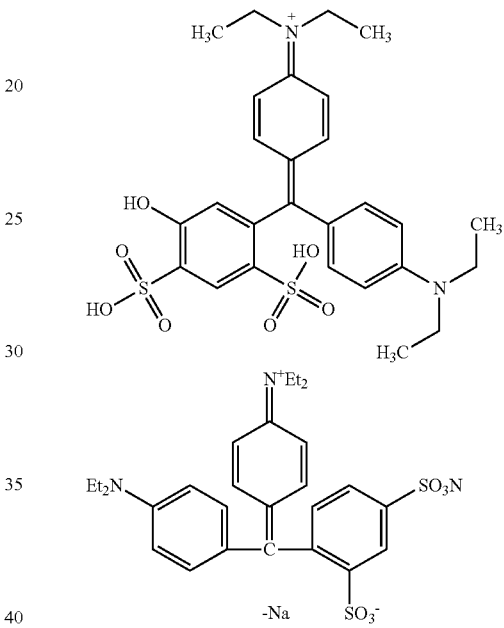

Each dendritic structure, or dendron, for generations higher than 1, comprises a structure of the type dendrons of Fréchet such as described in Dendrimers and other dendritic polymers, J. M. J Fréchet, D. A. Tomalia, Wiley, New York, 2001 having the following formula (D):

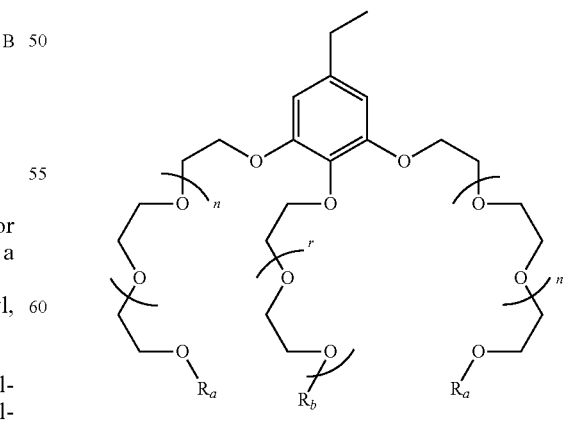

wherein $R_a$, $R_b$ and $R_c$ represent independently from each other, an linear or branched alkyl group, a biological molecule, a fluorophore or a dye, n is an integer comprised from 1 to 10 and r is an integer comprised from 1 to 20.

Thus, compounds according to the invention comprise a structure (D)m, wherein D comprises at least one ether of benzyl alcohol, said benzyl being substituted either at positions 3, 4 or 5, or at positions 3 and 5 by chains composed of oligoethyleneglycol patterns, and at least one of said chains being functionalized at its extremity by a biological molecule, a fluorophore or a dye and m=1, 2 or 4.

The inventors have found that compounds of formula I could be polyfunctionalized, i.e. they can bear several different biological molecules and/or different fluorophores and/or different dyes to detect specific cells, in particular cancer cells and in particular in the brain. Said polyfunctionalization leading for example to a specific recognition of cancer cells vis-à-vis of normal cells.

Another advantage of the invention is that the specific recognition of a cancer cells may lead to the specific delivery of an active principle to said cancer cell if the compound of formula I bear at least one active principle, such as an anticancer drug.

In an advantageous embodiment, compounds of formula (I) are functionalized by one or two or three biological molecules and/or fluorophores and/or dyes for generation 1, by one or two or three or four or five biological molecules and/or fluorophores and/or dyes for generation 2, by one or two or three or four or five or six or seven biological molecules and/or fluorophores and/or dyes for generation 3, and so on.

A nanoprobes bearing several biological molecules and/or fluorophores and/or dyes, identical or different, is liable to recognize specifically a tumor cell as tumor cell differ from normal cells only by an overexpression of cell markers If the recognition is specific, it allows treating specifically the tumor cell and not the normal cell and thus to decrease the toxicity of the therapy and/or increasing the radioactive doses and thus the efficacy of the treatment In an advantageous embodiment, the present invention relates to nanoprobes of formula I, defined above, characterized in that the group of formula (II) is complexed to a ligand or a radioelement to give a group of formula (III):

represents:

a metallic ion such as gadolinium or manganese, or a gamma radiation emitter radio-element or a position emitter radio-element such as $^{99m}$technetium, $^{64}$copper, $^{(67, 68)}$gallium, $^{124}$iodine, or an alpha or beta negative radiation emitter radio-element such as $^{177}$lutétium, $^{90}$yttrium, $^{166}$holmium or $^{186}$rhenium.

The metallic ion is used for MRI or Manganese-enhanced magnetic resonance imaging (MEMRI) as a diagnostic tool.

A gamma radiation emitter radio-element or a positon emitter radio-element is used in nuclear medicine, in particular gamma scintigraphy (GSc) and single photo emission computed tomography (SPECT) for gamma emitters, or positon emission tomography (TEP) for $\beta^+$ emitters as a diagnostic tool.

An alpha or beta negative radiation emitter radio-element is used for curietherapy.

Another advantage of the invention is the coupling of the recognition of specific cells by its polyethyleneglycol functionalized part, either with an imaging method for the localization and/or the diagnostic of pathology, or with a curing method such as curietherapy leading to the specific radiotherapy of cancer cells.

In an advantageous embodiment, the present invention relates to nanoprobes having a group of formula (II) complexed to a ligand to give a group of formula (III) defined above, characterized in that when the metallic ion is $^{99m}$technetium, $R_4$ and $R_6$ represent a chain A wherein n=1 and $R_a$ represents a tert-butyl, $R_5$ represent a chain A wherein r=1 and $R_b$ represents a N,N-diallyl-L-DOPA bonded by its carboxylic group, then the nanoprobe comprises at least another oligoethyleneglycol chain functionalized at its extremity by a group chosen among a biological molecule, a fluorophore, or a biocompatible dye.

The nanoprobe described below is thus preferably excluded from the scope of the invention:

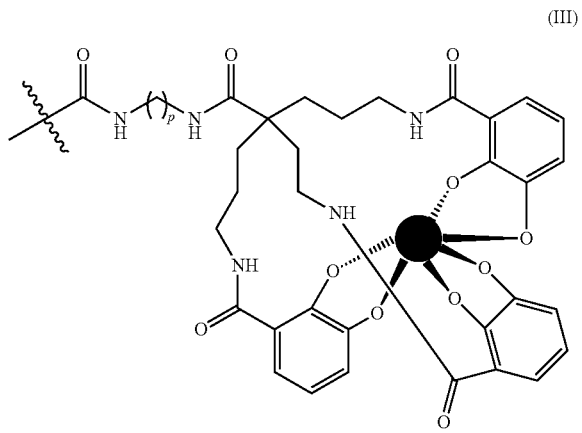

(III)

wherein

●

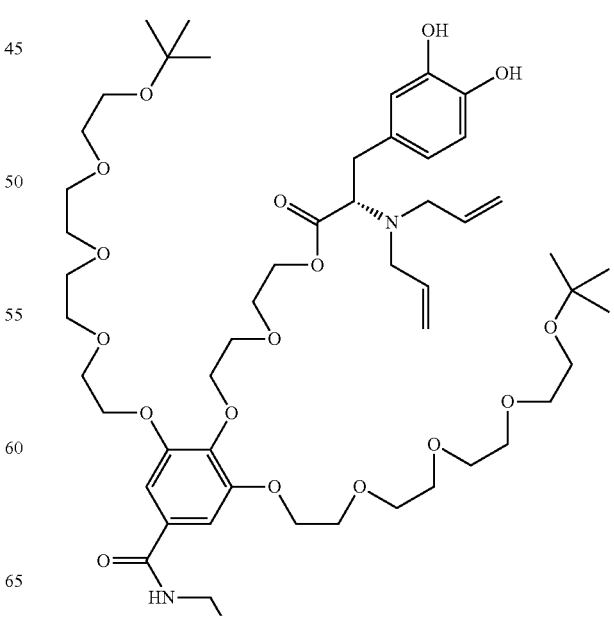

-continued

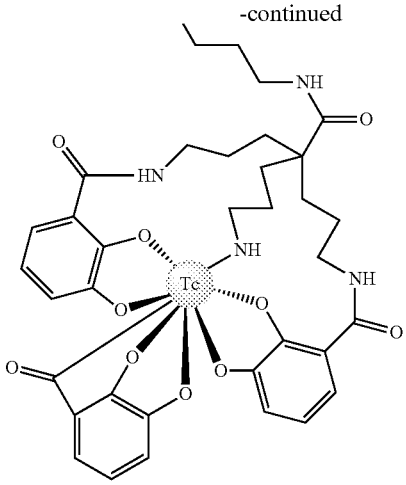

In an advantageous embodiment, the present invention relates to nanoprobes of formula I, having a group of formula (II) complexed to a ligand to give a group of formula (III), defined above, characterized in that their mean diameter is comprised from 2 to 60 nm, preferably from 15 to 50 nm, more preferably from 20 to 35 nm.

Another advantage of the invention is that once administered by an intraveinous route, nanoprobes present diffusion different from purely molecular edifice due to its small size. Once administered by an intradermal route, the nanoprobes will be drained by a lymphatic way up to the first filter i.e. a node that the nanoprobes will be liable to cross due to its small size and then the nanoprobes will be drained in the lymphatic system up to thoracic channel For the nanoprobes providing MRI contrast according to the invention, the relaxivity, that is an indicator of the efficacy as imaging agent of a compound, is equal or higher than the one of the prior art.

In an advantageous embodiment, the present invention relates to one of the nanoprobes defined above, characterized in that the formula (I) is chosen among the following formulae:

(Ia1)

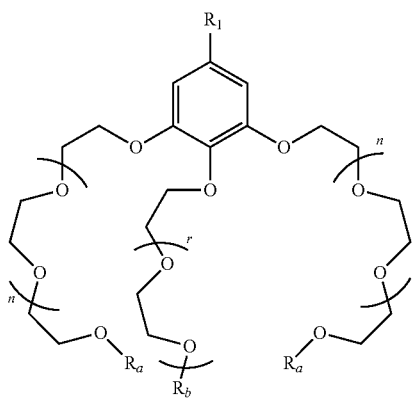

(Ia2)

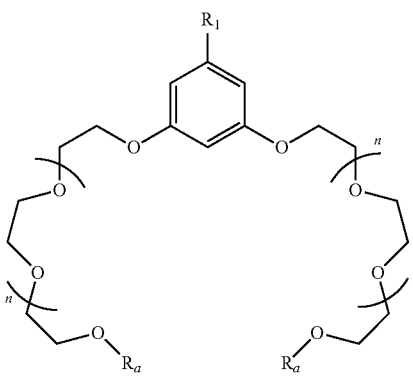

(Ib1)

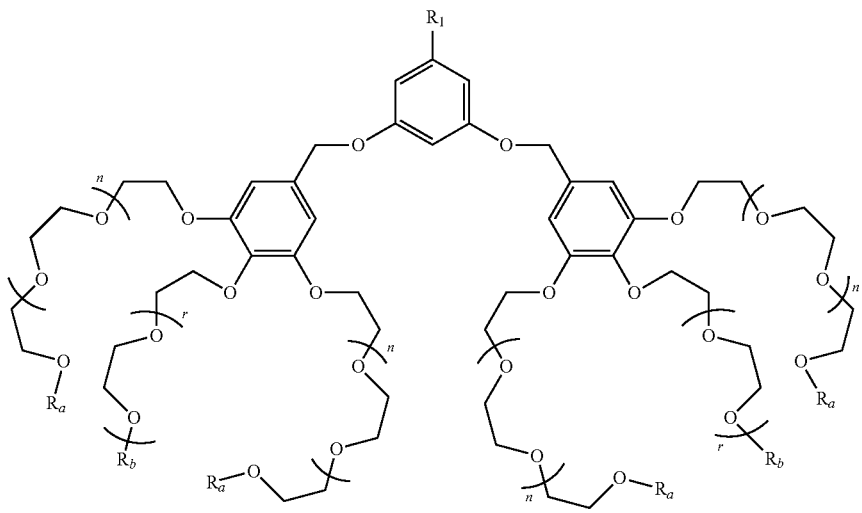

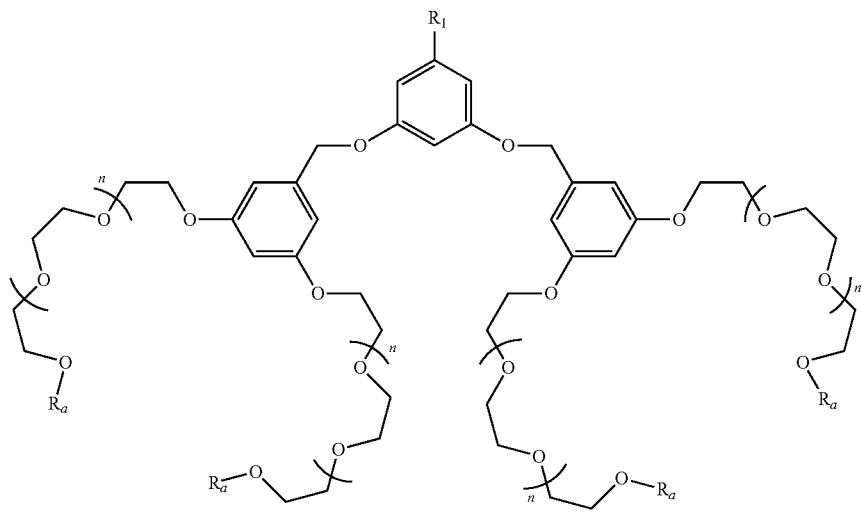
(Ib2)
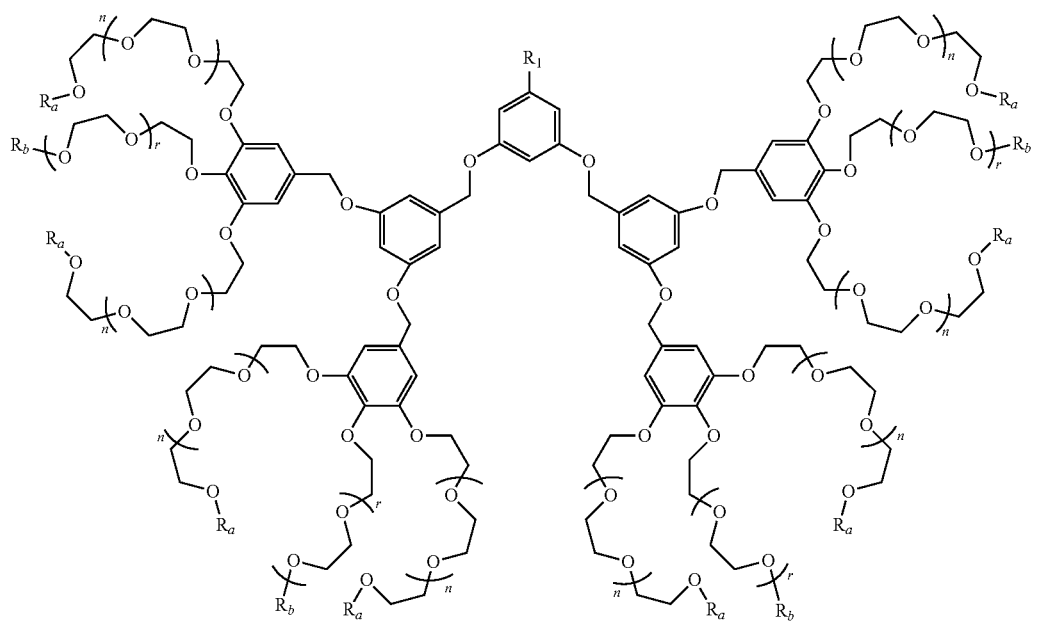
(Ic1)
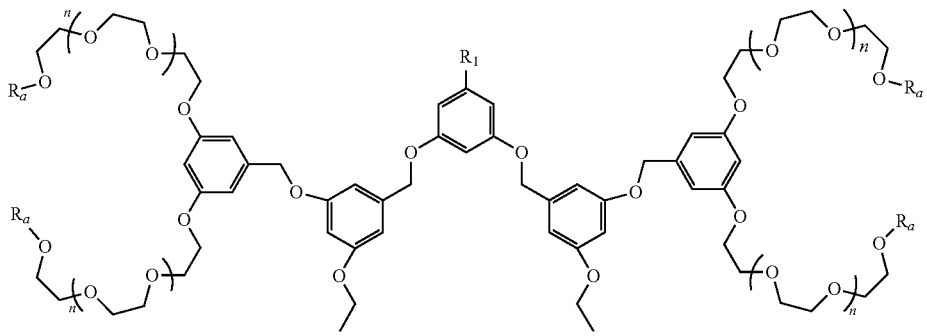
(Ic2)

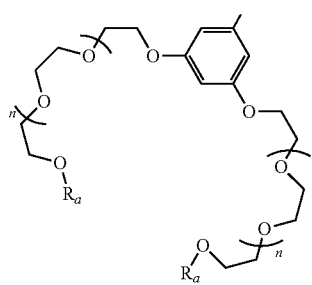 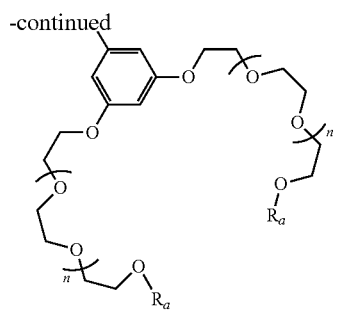

wherein $R_1$ represents a group X such as defined above, n is an integer comprised from 1 to 10, r is an integer comprised from 1 to 20, r being ≥n, and $R_a$ represents a group chosen among:
- a biological molecule, such as N,N-diallyl-L-DOPA, L-DOPA, an antibody, preferably a monoclonal antibody, in particular directed against antigens carried by tumor cells or tumor tissue, in particular anti-Ca15-3 or human Ipilimumab antibody, a peptide or any other vector such as an hormone in particular alpha melanocyte stimulating hormone (alpha-MSH), or heteroaromatic analog of iodo benzamide derivatives or quaternary ammoniums allowing the recognition of the nanoprobes by a cell, in particular a tumor cell, or
- a fluorophore or
- a biocompatible dye bearing at least one group —$SO_3R_3$ wherein $R_3$ represents an hydrogen, sodium or calcium atom and eventually one or more groups chosen among —OH and —$CO_2H$, or
- a linear or branched alkyl.

One of the advantages of the invention is to provide nanoprobes bearing in particular L-DOPA, liable to cross the blood brain barrier and to target specific receptors of the cancer cell, in particular neuroendocrine tumors or neuroblastomes.

One of the advantages of the invention is to provide nanoprobes bearing in particular N,N-diallyl-L-DOPA, the diallyl groups of which are removed in vivo leading to nanoprobes bearing in particular L-DOPA.

Antibody anti-Ca15-3 recognizes breast cancer cells.

Human Ipilimumab antibody is an anti CTLA-4 receptor antibody from Bristol Myers Squibb for the treatment of melanoma.

Quaternary ammoniums target proglycanes and allow detecting and treating cartilage tumors.

Therefore, the invention allows improving the diagnosis and staging of the tumor especially the node staging (by external detection with imaging of the tumor status of sentinel nodes) and proposes targeted therapy.

In an advantageous embodiment, the present invention relates to nanoprobes of formula (Ia1), (Ia2), (Ib1), (Ib2), (Id 1), (Ic2) defined above, chosen among the following formulae:

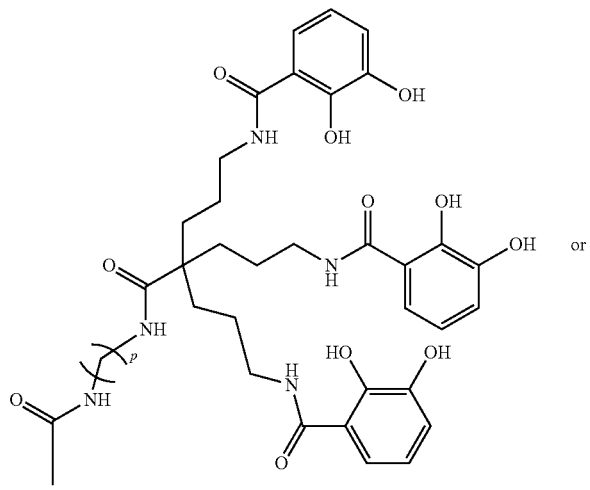

(Ia1a) or

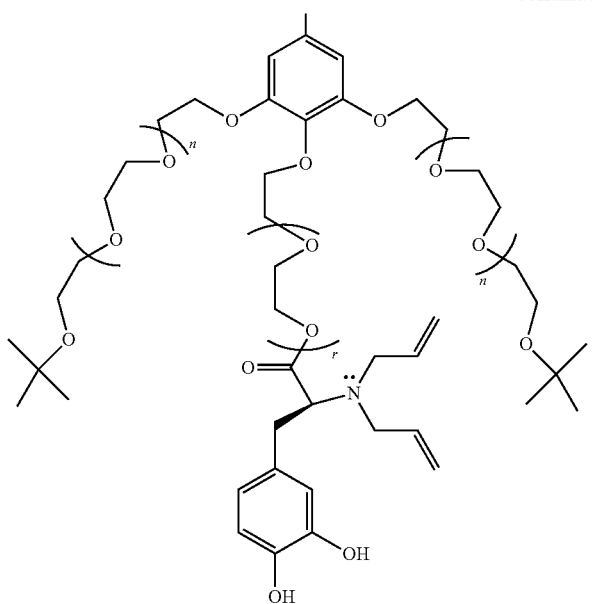
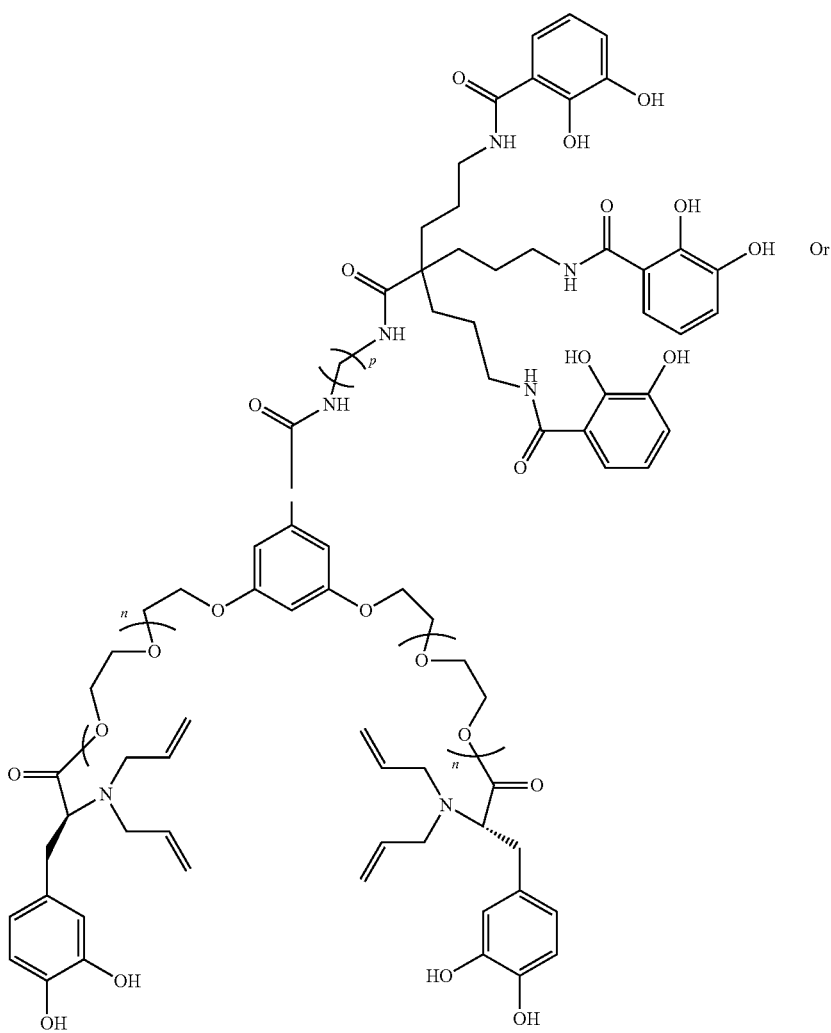
(Ia2a)

-continued
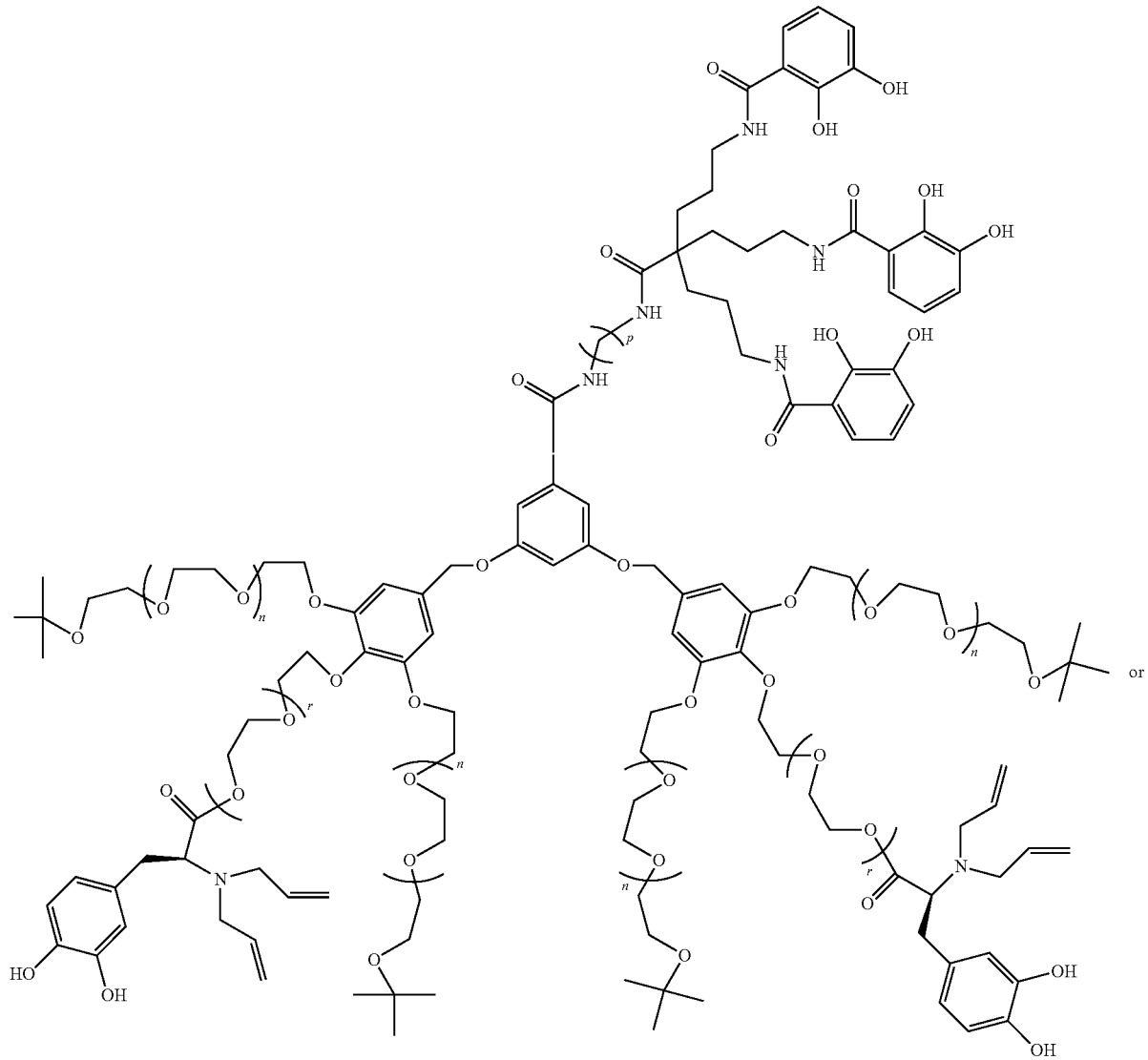
(Ib1a)
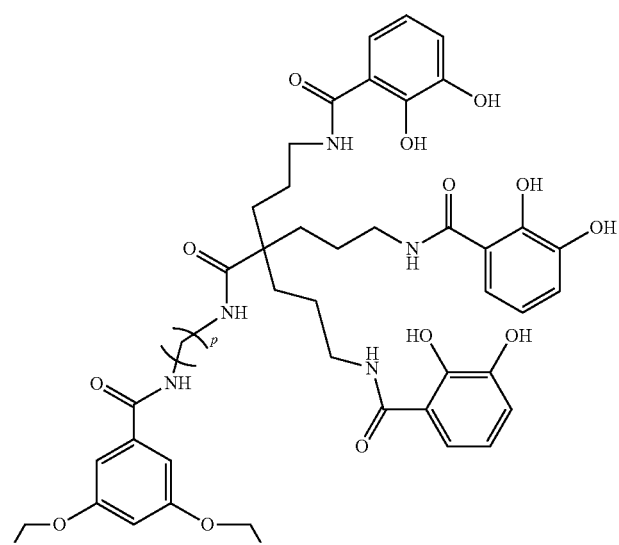
(Ib2a)

-continued

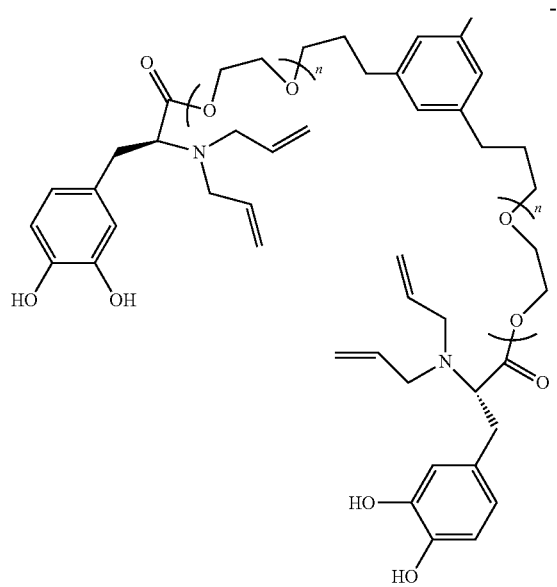
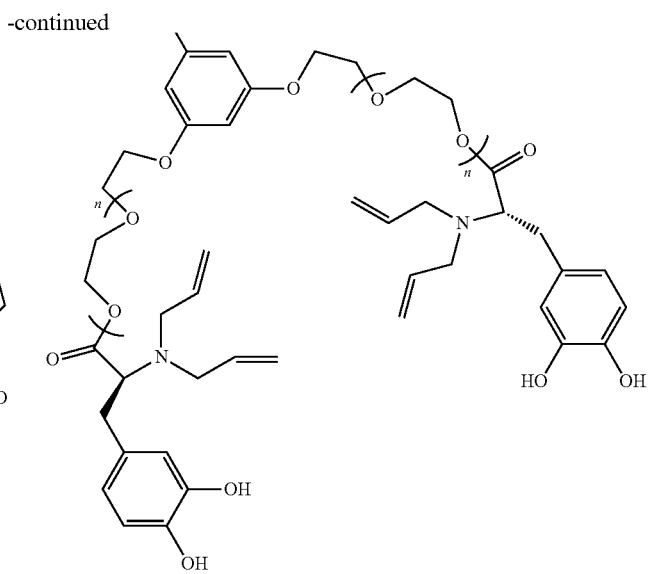

In an advantageous embodiment, the present invention relates to nanoprobes chosen among (Ia1a), (Ia2a), (Ib1a), or (Ib2a) comprising further a complexed $^{99m}$technetium.

In another aspect, the present invention relates to nanoprobes of formula (I) wherein X represents a group of formula (II) complexed to a ligand to give a compound of formula (III), for its use as a medicament, suitable especially for detecting and/or treating a cancer cell or tissue or organ.

In an advantageous embodiment, the present invention relates to nanoprobes of formula (I) wherein X represents a group of formula (II) complexed to a ligand to give a compound of formula (III), for its use as a medicament, suitable especially for detecting and/or treating a cancer cell or tissue or organ, wherein said cancer is brain cancer.

In an advantageous embodiment, the present invention relates to nanoprobes of formula (I) wherein X represents a group of formula (II) complexed to a ligand to give a compound of formula (III), for its use as a medicament, suitable especially for detecting and/or treating a cancer cell or tissue or organ, wherein said cancer is breast cancer and the organ is the sentinel node.

Another advantage of the invention is to provide nanoprobes bearing in particular several biological effectors in particular antitumor antibodies, liable to recognize a node comprising tumor cells, and/or a fluorophore and/or a dye. Thus, the nanoprobes allow identifying by an external route by imaging metastatic nodes, in particular the sentinel node before surgery and during surgery.

The knowledge before surgery of the tumor status of sentinel nodes allows adapting the surgical gesture to prevent a delayed second time of surgery or in contrast an usefulness node dissection.

Thus an negative imaging before the surgery avoid a node sampling that is useless and a positive imaging allows carrying out the lymph node dissection during the surgery of the primary tumor.

The liability to complex very simply a radio-element in the nanoparticles allows carrying out said complexation in a radio-pharmaceutical laboratory of a radio nuclear service.

Thus, with the nanoparticles of the invention, it is possible to carry out targeted metabolic radio therapy or curietherapy with a high specificity and the potential advantages of a nanoparticle (good diffusion, concentration effect higher than with a molecular radio-pharmaceutical. For instance, metabolic radiotherapy of hepatic tumors can be obtained by selective injection in the hepatic artery of nanoparticles complexed to toxic radio-elements (alpha or beta negative radiation emitter)

In another aspect, the present invention relates to pharmaceutical or diagnostic compositions comprising nanoprobes of formula (I) wherein X represents a group of formula (II) complexed to a ligand to give a compound of formula (III).

In an advantageous embodiment, the pharmaceutical composition is liable to be administered i.v.

In an advantageous embodiment, the pharmaceutical composition is liable to be administered p.o.

Doses can be easily determined by the one skilled in the art.

The invention will be illustrated by the FIGS. 1A-E to 9 and examples 1 and 2 below.

No adverse side-effect was observed after intraveinous (IV) injection in rats and mice.

Planar dynamic acquisition acquired just after intra-venous injection in right saphene vein:
FIG. A: 10 sec image at 1 min post-injection;
FIGS. B and C—30 sec
Images respectively 10 and 20 minutes after injection of 20 MBq of 99mTc-Dopadendron
(K=kidney activity, SI=injection site, C=cardiac activity, L=liver activity);
FIGS. D and E: SPECT-CT images acquired at 30 min to 1 H30 after injection (FIG. D=posterior projection, FIG. E=left oblique posterior projection).

FIGS. 1A to 1E show a rapid vascular dispersion, a low liver uptake, a rapid and intense renal activity. Vascular activity persisted 20 minutes after IV injection. SPECT revealed a digestive uptake, such as observed in human after injection of 18F-Dopa. One hour after injection, liver and vascular activity have disappeared, and only renal uptake was intense. No reticuloendothelial system (RES) uptake was observed.

Figure 1:
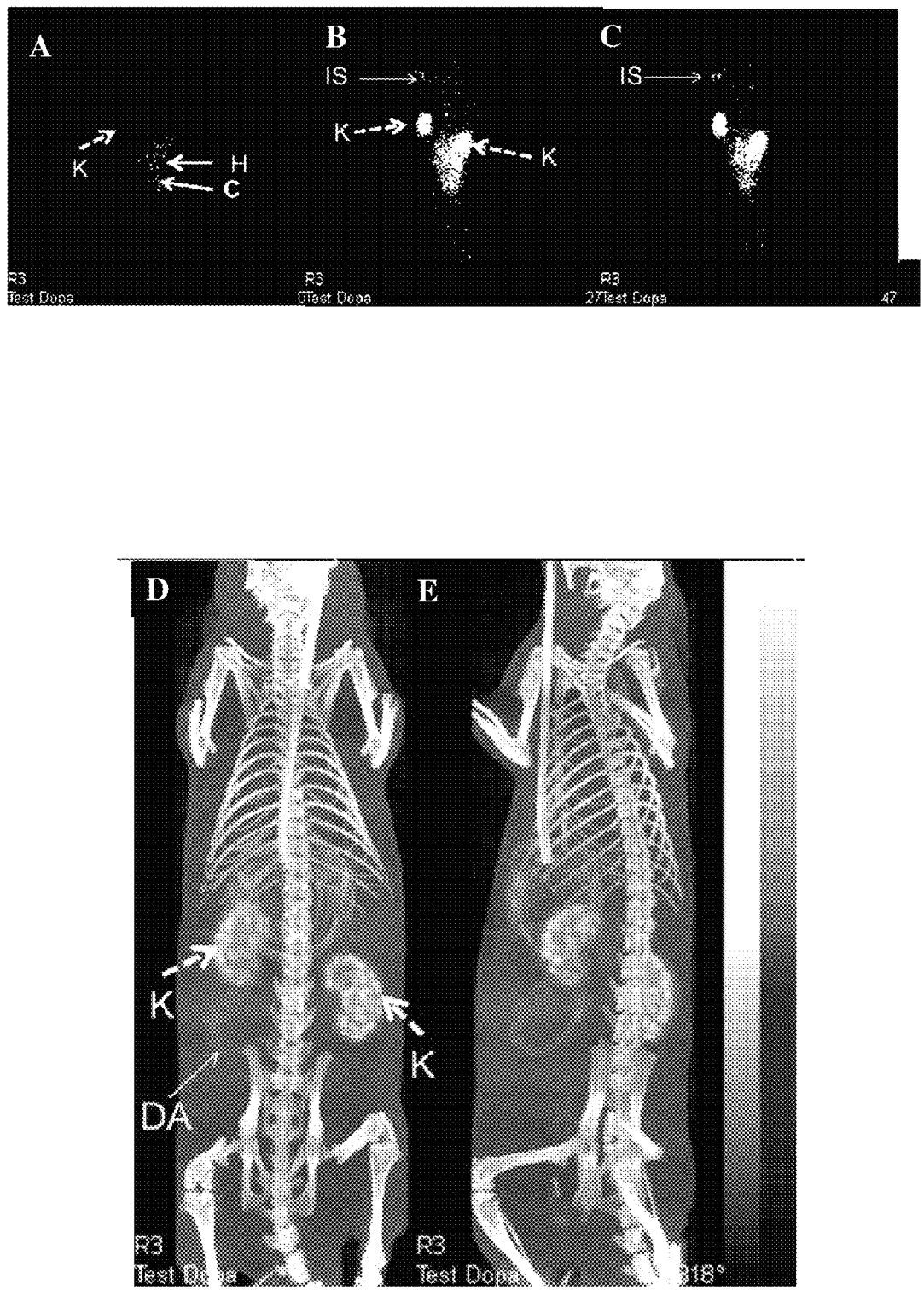
FIGS. 1A to 1E present the scintigraphic imaging (Single Photon Emission Computed Tomography SPECT) obtained with the nanoprobe (Ia1a) after intraveinous injection in rats at a dose of 20 MBq of 99mTc-Dopadendron (Ia1a).
Figure 2:
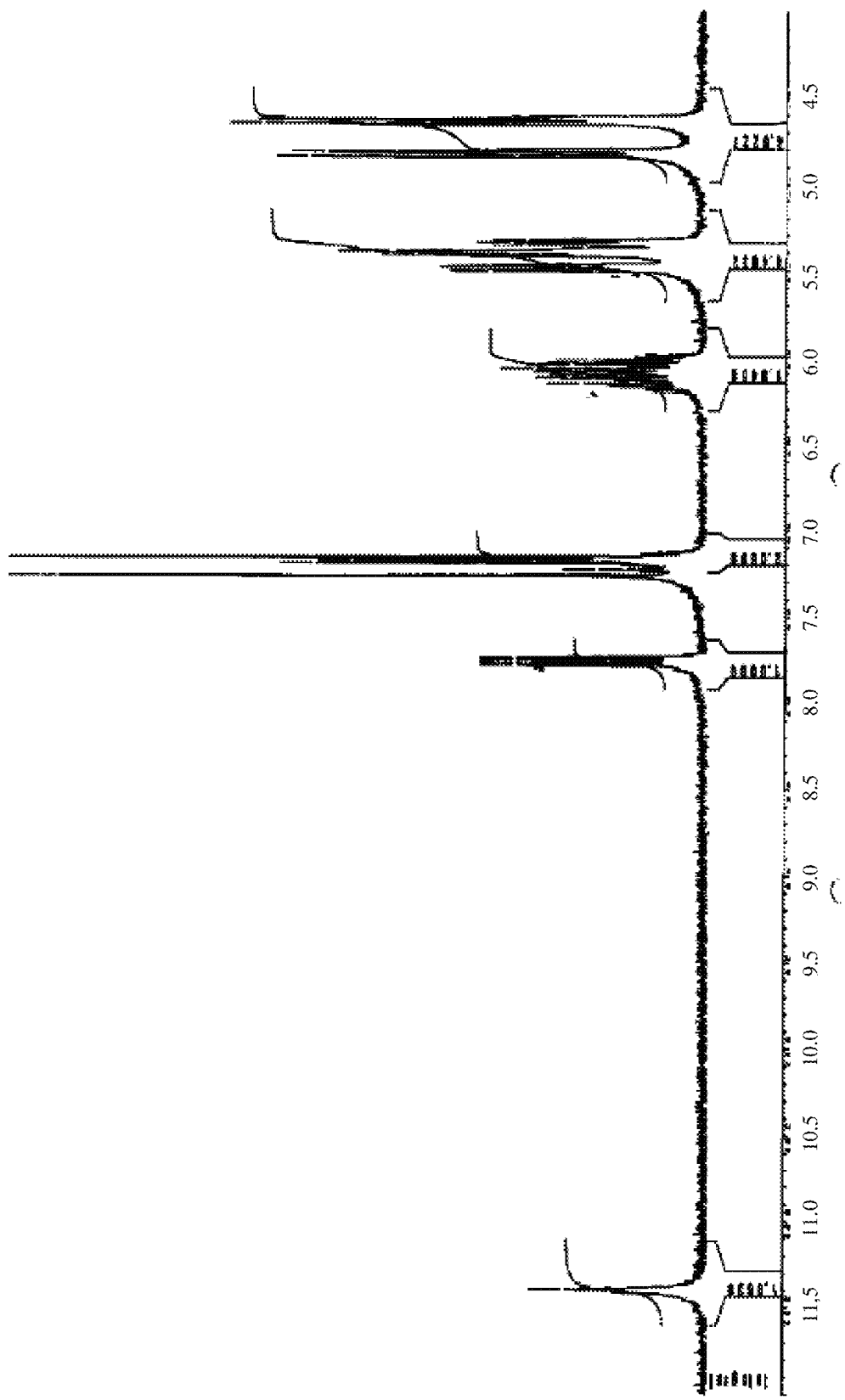

FIG. 2 presents the $^1$H NMR (300 Mhz, CDCl$_3$) of allyl-protected compound 3.

Figure 3:
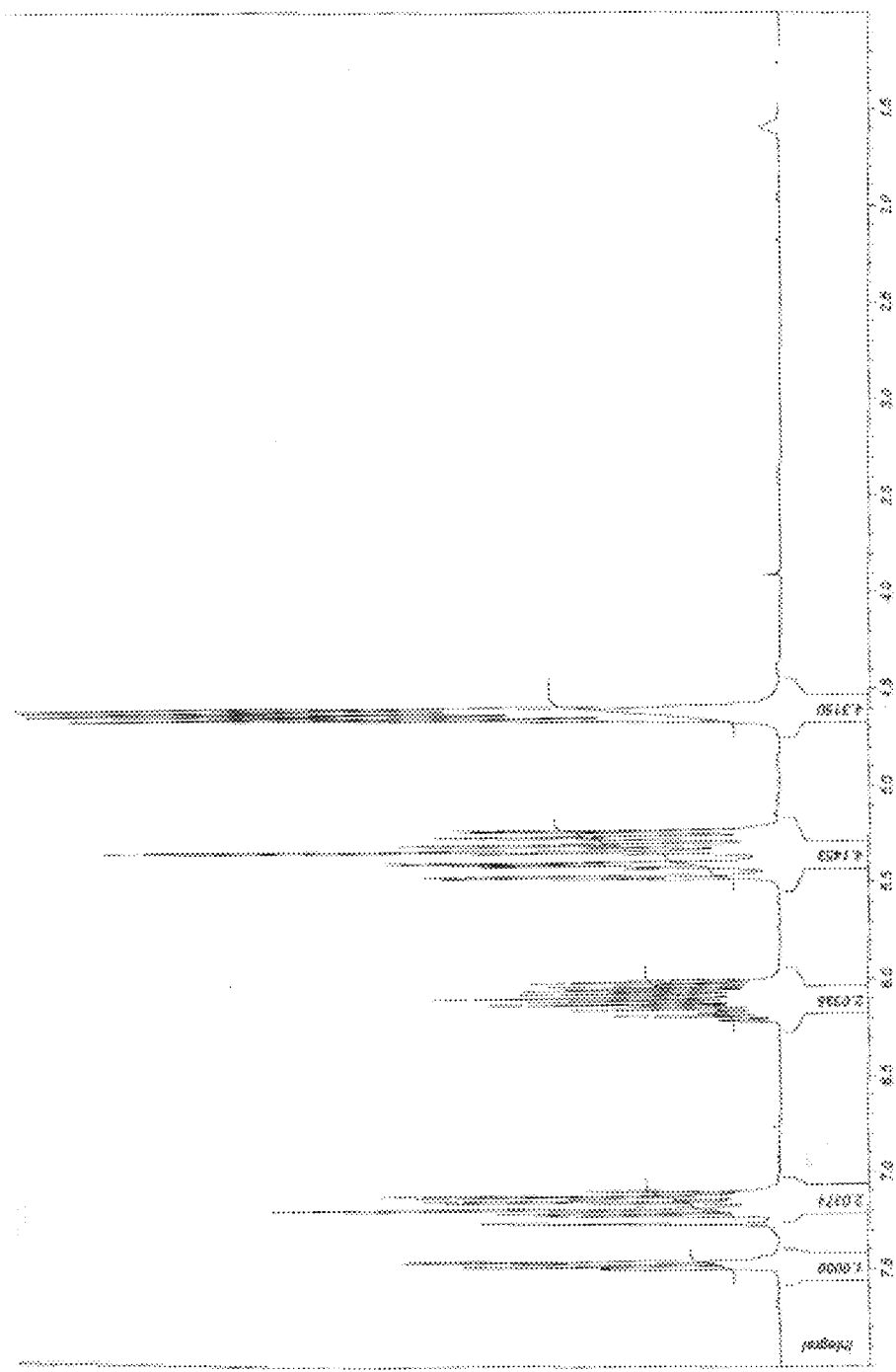

FIG. 3 presents the $^1$H NMR (300 Mhz, CDCl$_3$) of allyl-protected compound 4.

Figure 4:

FIG. 4 presents the $^1$H NMR (300 Mhz, CDCl$_3$) of compound 6.

Figure 5:
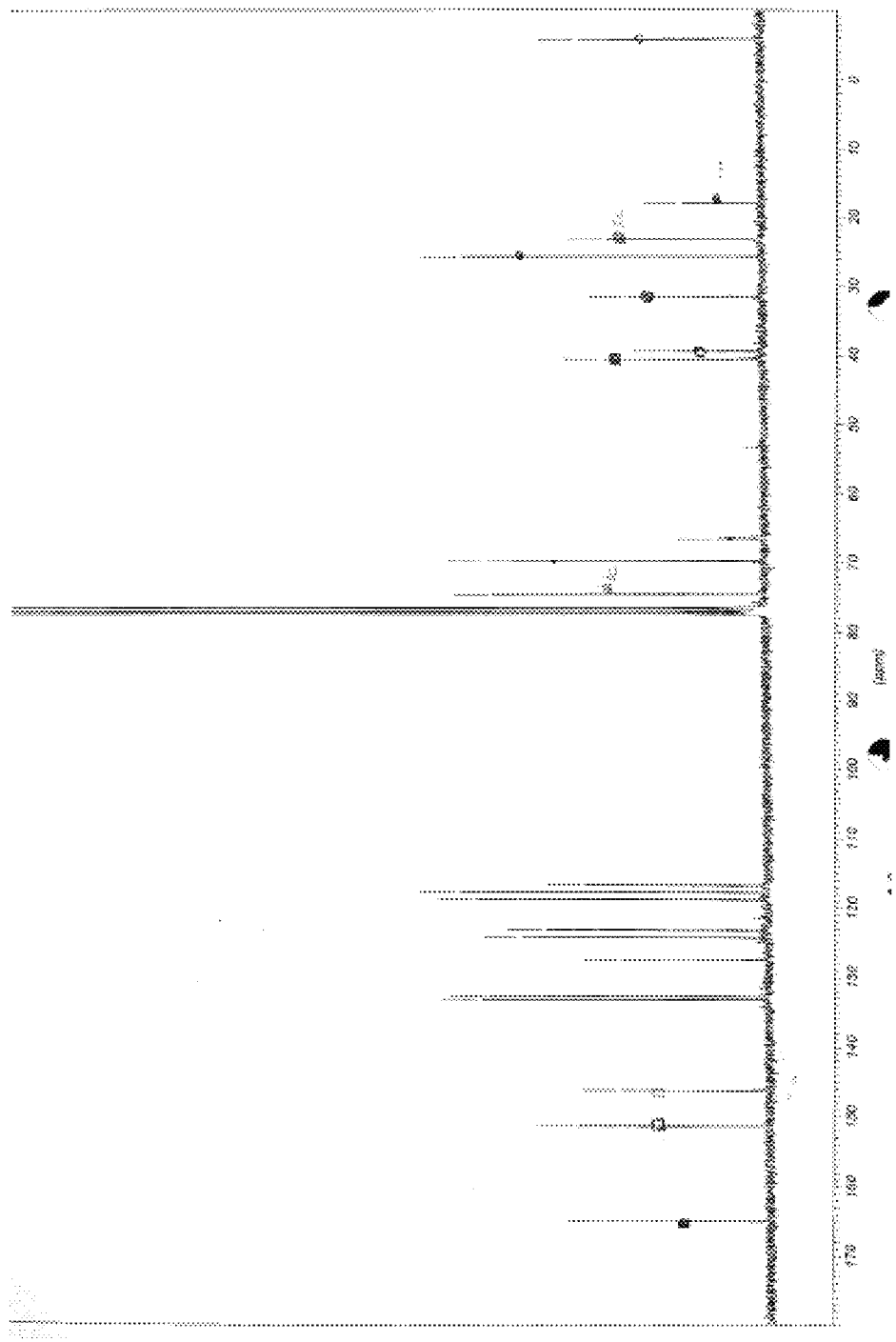

FIG. 5 presents the $^{13}$C NMR (75 Mhz, CDCl$_3$) of compound 6.

Figure 6:
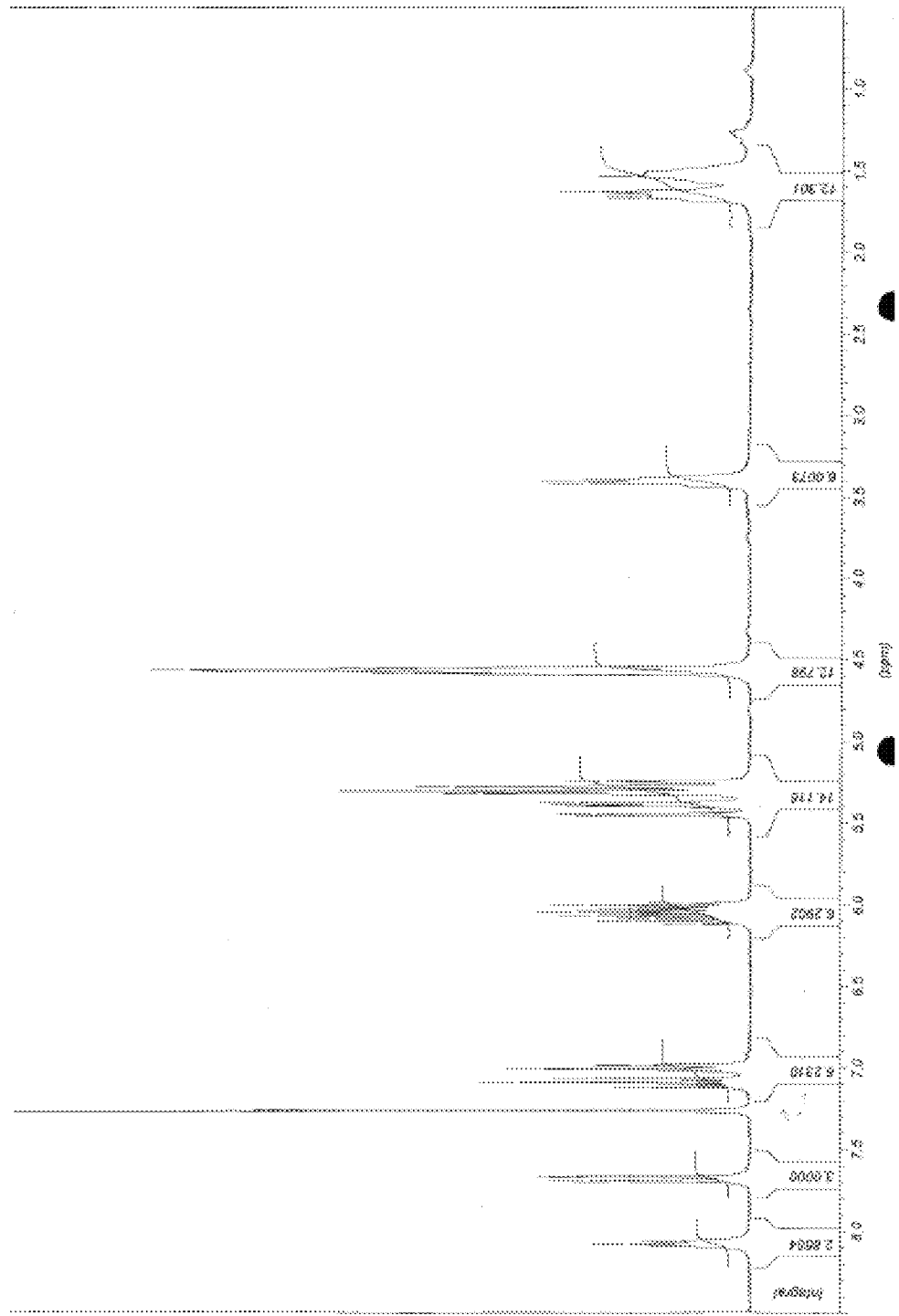

FIG. 6 presents the $^1$H NMR (300 Mhz, CDCl$_3$) of compound 9.

Figure 7:
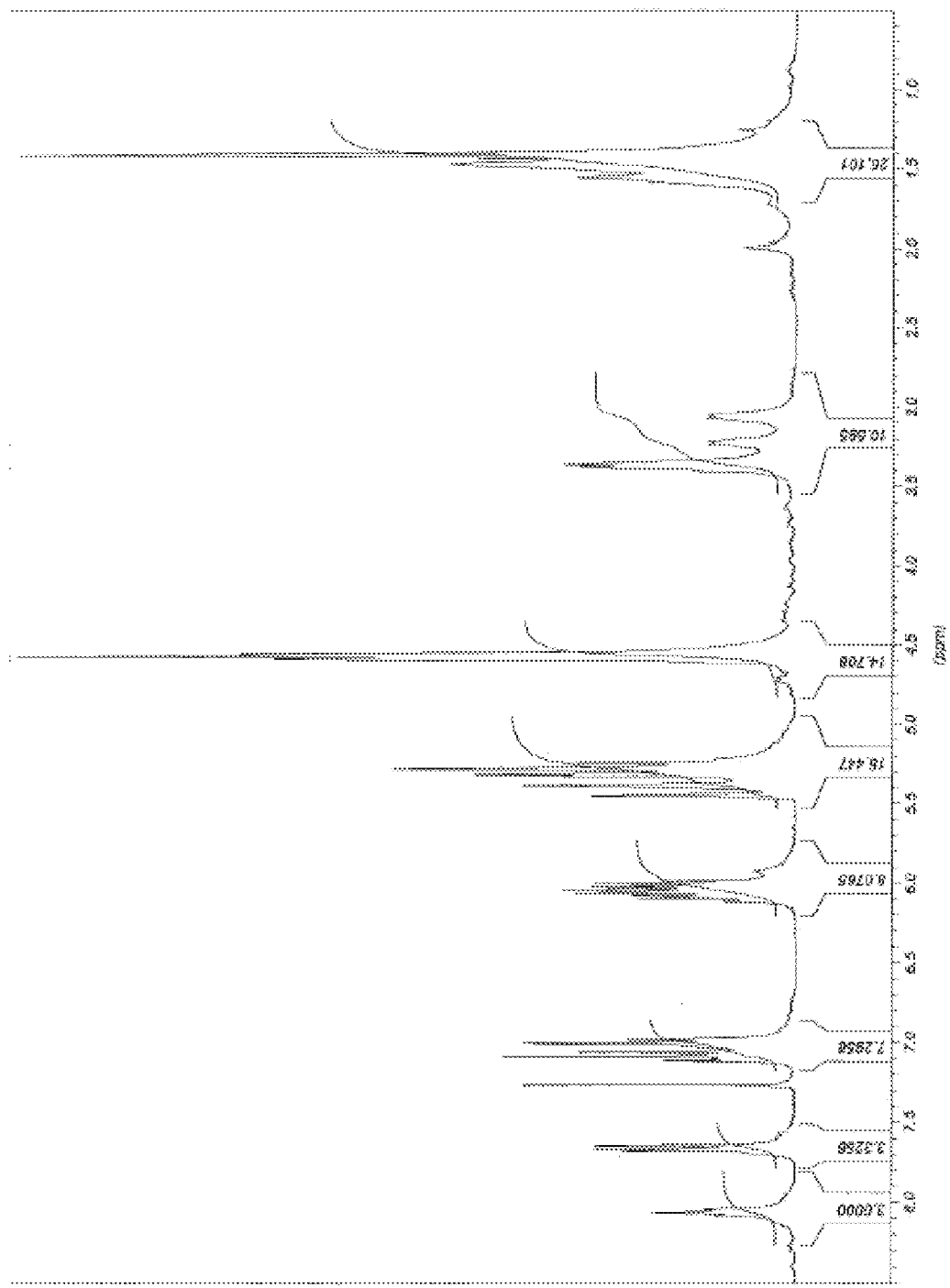

FIG. 7 presents the $^1$H NMR (300 Mhz, CDCl$_3$) of compound 11.

Figure 8:
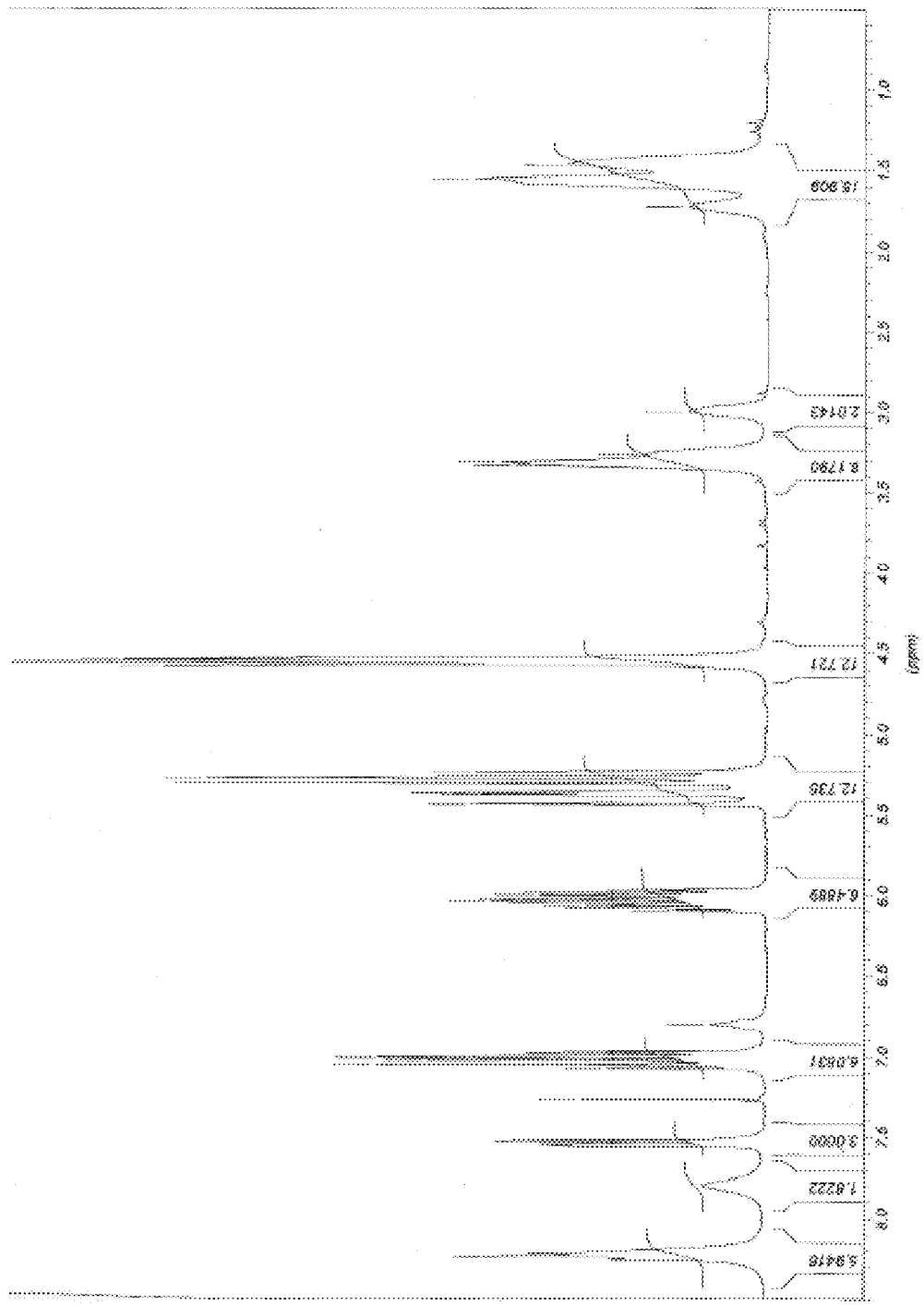

FIG. 8 presents the $^1$H NMR (300 Mhz, CDCl$_3$) of compound 12.

Figure 9:
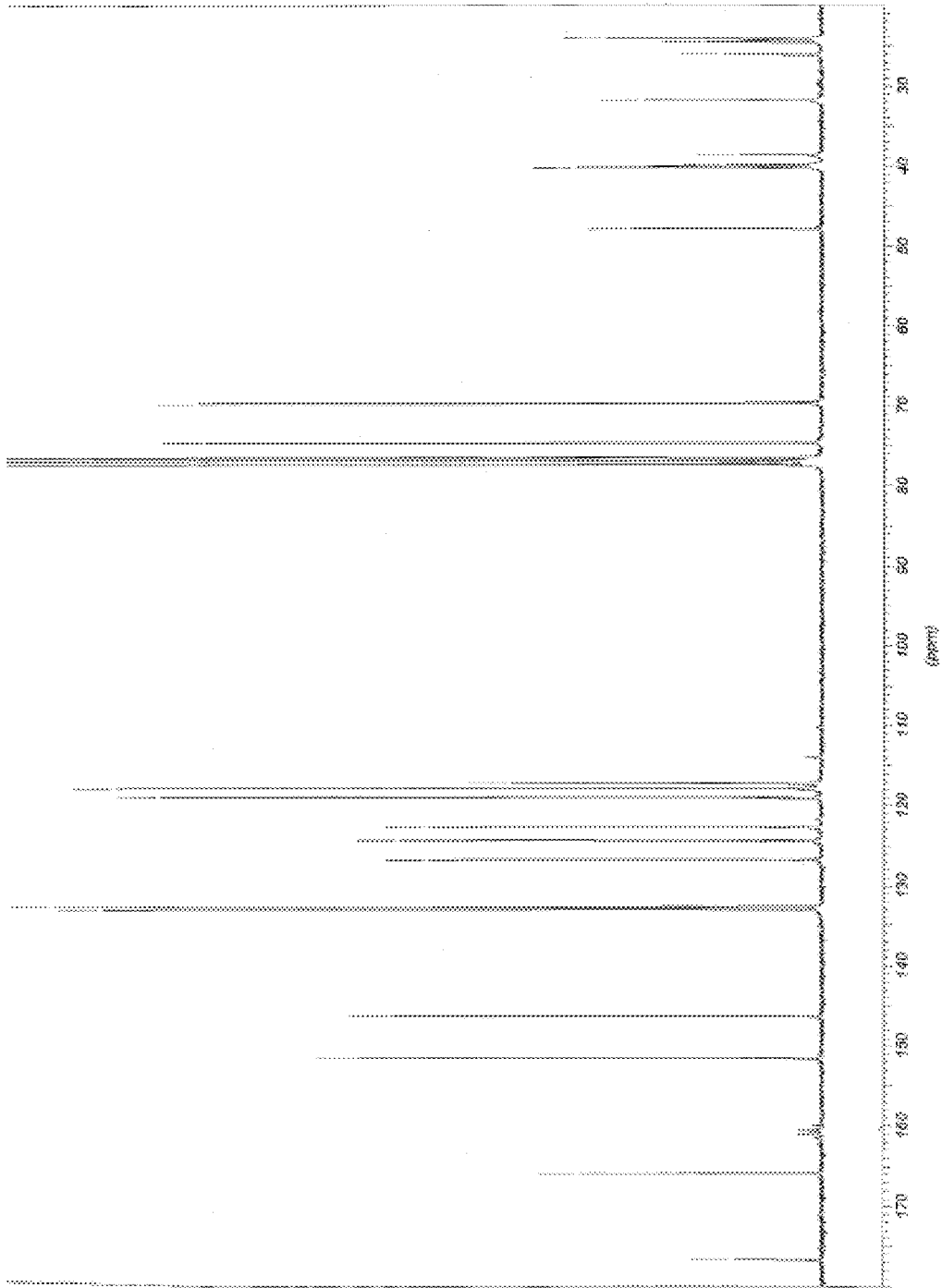

FIG. 9 presents the $^{13}$C NMR (75 Mhz, CDCl$_3$) of compound 12.

EXAMPLES

Example 1

Synthesis of Nanoprobes Ia1a Wherein n=2 Complexed with $^{99}$mTc

Example 1.1

Catechol Synthesis

Catechol has been synthesized according to scheme I:

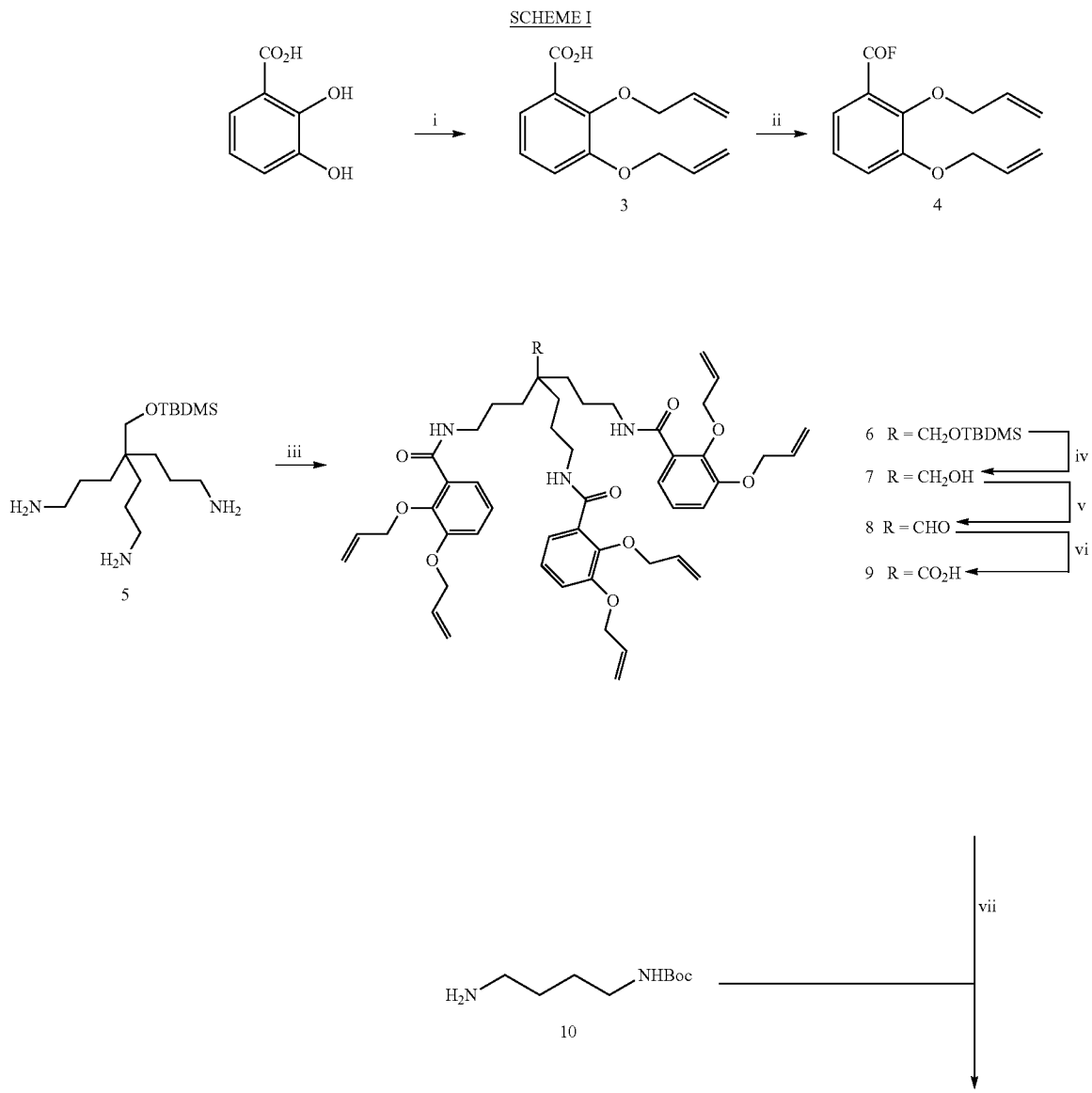

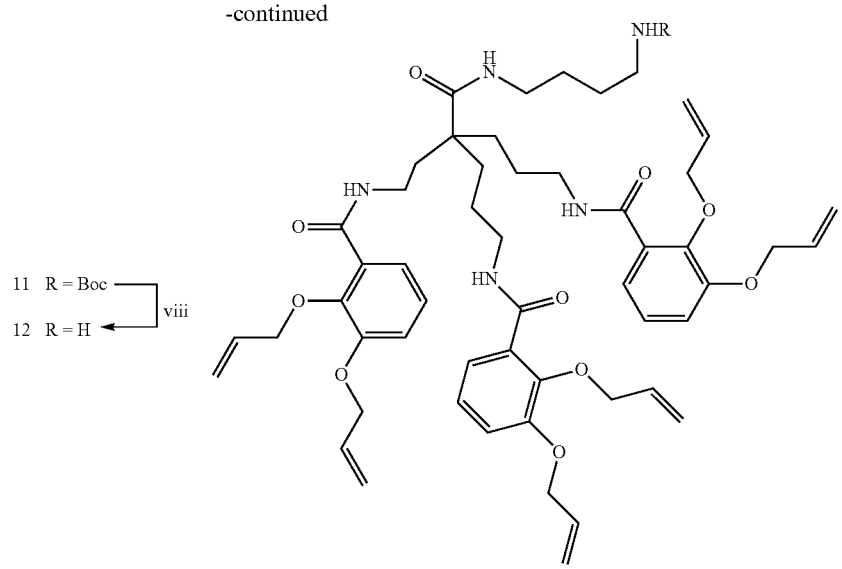

11 R = Boc
12 R = H  ⟵viii

Materials and Synthesis:

Reagents and solvents were purchased reagent grade and used without further purification.

Compounds 5[1], 10[2] and 13[3] were prepared according to the literature (respectively: [1]: D. Imbert, F. Thomas, P. Bare!, G. Serratrice, D. Gaude, J.-L. Pierre, J.-P. Laulhère, New J. Chem. 2000, 24, 281-288; [2]: M. Ou, X. L. Wang, R. Xu, C. W. Chang, D. A. Bull, S. W. Kim, Bioconj. Chem., 2008, 19, 626-633; [3]: A. Bertin, 1. Steibel, A.-I. Michou-Gallani, J.-L. Gallani, D. Felder-Flesch, Bioconj. Chem. 20, 760-767).

All reactions were performed in standard glassware under Ar and solvents were, if necessary, purified by standard procedures prior to use. Evaporation and concentration were done at water-aspirator pressure and drying in vacuo at $10^{-2}$ Torr (1.33 Pa). Column chromatography: silica gel 60 (230-400 mesh, 0.040-0.063 mm) from E. Merck. NMR spectra: Bruker AM-300 (300 MHz); solvent peaks as reference; δ in ppm.

Compound 3:

a solution of 2,3-dihydroxybenzoïc acid (10.00 g, 64.89 mmol) and $K_2CO_3$ (33.20 g, 240.07 mmol) in acetonitrile (140 mL) was heated at 80° C. for 1 h. The reaction mixture was then cooled to room temperature and a solution of allyl bromide (20.80 mL, 240.07 mmol) in acetonitrile (80 mL) was added drop wise. The resulting mixture was heated 17 h at 70° C. and filtered. The filtrate was evaporated to dryness and diluted in EtOH (100 mL). After adding a solution of NaOH (7.40 g, 184.92 mmol) in 12 mL water, the reaction mixture was refluxed for 23 h and evaporated to dryness. The so-obtained residue was dissolved in $CH_2Cl_2$ (100 mL) and 150 mL of HCl 1 N were added. The aqueous sub phase was extracted two times by using $CH_2Cl_2$ (200 mL) and the organic phases put together, washed twice with water (200 mL), dried ($MgSO_4$), filtered and evaporated. After recristallisation in a mixture hexane/ether (50 mL/50 mL), compound 3 (9.88 g, 42.18 mmol) was obtained with 65% yield. White powder. M.p 138° C. $^1H$ NMR ($CDCl_3$): 4.62 (d, $^3J=5$ Hz, 2H), 4.82 (d, $^3J=6$ Hz, 2H), 5.32-5.50 (m, 4H), 6.01-6.15 (m, 2H), 7.16 (m, 2H), 7.75 (dd, $^3J=6$ Hz, IH); $C_{13}H_{14}O_4$: calc. C, 66.66; H, 6.02; O, 27.32. found C, 66.58; H, 6.02; O, 27.40.

Compound 4:

0.51 mL (5.977 mmol) of trifluorotriazine were added to a stirred solution of 3 (2.00 g, 8.54 mmol) in dry $CH_2Cl_2$ (100 mL) cooled to 0° C. The mixture was stirred 10 min before addition of an anhydrous $CH_2Cl_2$ (30 mL) solution of pyridine (0.76 mL, 9.39 mmol). After 17 h at room temperature, the mixture was washed with cold water (2×75 mL) and NaCl saturated water (75 mL). The organic sub phase was then dried ($MgSO_4$) filtered and evaporated. Crude compound 4 was obtained as brown oil (1.82 g, 7.69 mmol) with 90% yield and used in next step without further purification. $^1H$ NMR ($CDCl_3$): 4.60-4.66 (m, 4H), 5.23-5.48 (m, 4H), 6.00-6.19 (m, 2H), 7.09-7.22 (m, 2H), 7.49 (d, $^3J=9$ Hz, IR); $^{13}C$ NMR ($CDCl_3$): 70.03, 75.02, 117.95, 118.42, 120.32, 123.99, 124.10, 132.46, 133.55, 150.50, 152.76, 157.46.

Compound 6:

Compound 4 (4.96 g, 21.00 mmol) in freshly distilled $CH_2Cl_2$ (100 mL) was added dropwise over 90 min to a stirred solution of N,N-diisopropylethylamine (4.52 mL, 27.36 mmol) and 5 (2.11 g, 6.36 mmol) in freshly distilled $CH_2Cl_2$ (100 mL) kept under nitrogen. After 60 h stirring at room temperature, the crude mixture was filtered, washed with water, dried (MgS04), filtered and then evaporated to dryness. Column chromatography ($SiO_2$, $CH_2Cl_2$/1% MeOH) allowed to obtain compound 6 (6.05 g, 6.17 mmol) in 97% yield. Pale yellow oil. $^1H$ NMR ($CDCl_3$): −0.01 (s, 6H), 0.82 (s, 9H), 1.25-1.48 (m, 12H), 3.29 (s, 2H), 3.34-3.38 (m, 6H), 4.57 (d, 12H), 5.24-5.46 (m, 12H), 6.00-6.12 (m, 6H), 6.99 (d, 3 J=13 Hz, 3H), 7.03 (d, $^3J=9.7$ Hz, 3H), 7.68 (d, $^3J=9$ Hz, 3H), 8.02 (t, 3H); $^{13}C$ NMR ($CDCl_3$): 5.67, 18.06, 23.35, 25.76, 31.48, 39.38, 40.54, 66.51, 69.77, 74.59, 116.75, 117.67, 118.76, 123.17, 124.23, 127.50, 132.80, 133.19, 146.24, 151.48, 164.98; $C_{56}H_{77}N_3O_{10}Si$. ½ $H_2O$: calc. C, 68.09; H, 7.90; N, 4.26. found C, 68.23; H, 7.83; N, 4.12.

Compound 7:

Compound 6 (735 mg, 0.75 mmol) was dissolved in 10 mL THF at 0° C. Tetra-n-butylammonium fluoride (2.21 mmol) was slowly added and the reaction mixture was heated at reflux for 3 h. The solution was evaporated and the so-obtained residue was dissolved in $CH_2Cl_2$ (100 mL), washed with water, dried ($MgSO_4$), filtered and evaporated. Column chromatography ($SiO_2$, $CH_2Cl_2$/3% MeOH) afforded 7 (610 mg, 0.71 mmol) in 94% yield. Yellow oil. $^1H$ NMR ($CDCl_3$): 1:1.27-1.63 (m, 12H), 3.39 (m, 8H), 4.58 (d, 12H), 5.26-5.46 (m, 12H), 6.00-6.12 (m, 6H), 7.02 (d, $^3J=8$. Hz, 3H), 7.12 (t, $^3J=8$ Hz, 3H), 7.68 (d, $^3J=9$ Hz, 3H), 8.08 (t, $^3J=5$ Hz, 3H), $^{13}C$ NMR ($CDCl_3$): 23.27, 31.14, 39.41, 40.43, 66.39, 69.76, 74.63, 116.78, 117.73, 118.87, 123.13, 124.37, 127.39, 132.78, 133.21, 146.24, 151.48, 158.25, 165.18; $C_{50}H_{63}N_3O_{10}$: calc. C, 69.34; H, 7.33. found C, 69.04; H, 7.78.

Compound 8:

A solution of anhydrous dimethyl sulfoxide (144 mL, 2.03 mmol) in 300 μL dry dichloromethane was added to a solution of oxalyl chloride (89 μL, 1.02 mmol) in freshly distilled dichloromethane (1 mL) kept at −60° C. The mixture was stirred for 15 min and then a solution of 7 (0.80 g, 0.92 mmol) in dry dichloromethane (3 mL) was added within a 10 min period; the solution obtained was stirred for an additional 1 h and the reaction mixture was allowed to warm to −30° C. N, N-diisopropylethylamine (10 eq.) was added and the reaction mixture was allowed to warm to room temperature. Water (50 mL) and dichloromethane (50 mL) were added and the organic layer was washed with brine, dried (MgS04), filtered and evaporated to dryness. Compound 8 was used in the next step without further purification. Colourless oil. $^1H$ NMR ($CDC_3$): 1.26-1.58 (m, 12H), 3.40 (m, 6H), 4.58 (d, 12H), 5.26-5.47 (m, 12H), 6.02-6.11 (m, 6H), 7.01 (d, $^3J=9$ Hz, 3H), 7.11 (t, $^3J=8$ Hz, 3H), 7.68 (d, $^3J=7$ Hz, 3H), 8.08 (t, 3H), 9.42 (s, IH); $^{13}C$ NMR ($CDCl_3$): 23.72, 29.30, 39.93, 51.29, 69.75, 74.49, 116.86, 117.71, 118.79, 123.09, 124.27, 127.20, 132.74, 133.15, 146.25, 151.46, 165.13, 206.59.

Compound 9:

Sulfamic acid (466 mg, 4.80 mmol) and then sodium chlorite (434 mg, 4.80 mmol) were added to a stirred solution of 8 (3.19 g, 3.69 mmol) in a mixture THF/water (1/1). After 13 h stirring at room temperature, 200 mL $CH_2Cl_2$ and 200 mL water were added and the resulting organic layer was washed with brine, dried ($MgSO_4$), filtered and evaporated to dryness. Column chromatography ($SiO_2$, $CH_2Cl_2$/3% MeOH) afforded 9 (0.47 g, 0.53 mmol) with 58% yield over the two steps. Pale yellow oil. $^1H$ NMR ($CDCl_3$): 1.53-1.66 (m, 12H), 3.40 (d, 6H), 4.57 (d, 12H), 5.24-5.45 (m, 12H), 5.99-6.12 (m, 6H), 6.98 (d, $^3J=9$ Hz, 3H), 7.09 (t, $^3J=8$ Hz, 3H), 7.68 (d, $^3J=9$ Hz, 3H), 8.08 (t, 3H); $^{13}C$ NMR ($CDCl_3$): 24.16, 31.92, 40.02, 48.06, 69.76, 74.64, 116.80, 117.72, 118.96, 123.12, 124.25, 127.34, 132.79, 133.16, 146.25, 151.48, 165.19, 178.96; $C_{49}H_{61}N_3O_{11}$·1.5$H_2O$: calc. C, 66.23; H, 7.06; N, 4.63; O, 22.08%. found C, 66.43; H, 6.83; N, 4.31; O, 22.43.

Compound 11:

A mixture of DCC (112 mg, 0.55 mmol) and DMAP (11 mg, 0.09 mmol) in dry $CH_2Cl_2$ (5 mL) and a solution of 109 (85 mg, 0.46 mmol) in dry $CH_2Cl_2$ (5 mL) were added to 9 (400 mg, 0.46 mmol) dissolved in freshly distilled dichloromethane (10 mL). A catalytic amount of HOBt was then added and the mixture obtained was stirred for 60 h at room temperature before filtration and evaporation to dryness. Column chromatography ($SiO_2$, $CH_2Cl_2$/3% MeOH) afforded 11 (455 mg, 0.44 mmol) in 97% yield. Pale yellow oil. $^1H$ NMR ($CDCl_3$): 1.41-1.55 (m, 25H), 3.07 (d, $^3J=5$ Hz, 2H), 3.23 (d, $^3J=5$ Hz, 2H), 3.37 (d, 6H), 4.56 (d, 12H), 5.24-5.45 (m, 12H), 5.98-6.11 (m, 6H), 6.98 (d, $^3J=9$ Hz, 3H), 7.09 (t, $^3J=8$ Hz, 3H), 7.66 (d, $^3J=9$ Hz, 3H), 8.04 (t, $^3J=11$ Hz, 3H), $^{13}C$ NMR ($CDCl_3$). 24.28, 25.57, 26.83, 27.53, 28.40, 32.21, 40.00, 47.87, 69.77, 74.65, 116.82, 117.73, 118.96, 123.06, 124.25, 127.36, 132.77, 133.19, 146.26, 151.49, 156.14, 165.21, 175.60; $C_{59}H_{79}N_5O_{12}$·MeOH: calc. C, 66.58; H, 7.73; N, 6.47; O, 19.22. found C, 66.77; H, 7.75; N, 6.63; O, 18.85.

Compound 12:

TFA (68 mL, 0.89 mmol) was added to a solution of 11 (465 mg, 0.44 mmol) in dry $CH_2Cl_2$ (10 mL). After 6 h stirring at reflux, the reaction mixture was evaporated and filtered on a silica pad ($SiO_2$, $CH_2Cl_2$/5% MeOH). Compound 12 (376 mg, 0.40 mmol) was obtained as a white foam in 90% yield. H NMR ($CDCl_3$): 1.46-1.73 (m, 16H), 2.99 (d, 2H), 3.26-3.32 (m, 8H), 4.56 (d, 12H), 5.23-5.43 (m, 12H), 5.96-6.09 (m, 6H), 6.98 (d, $^3J=9$ Hz, 3H), 7.06 (t, $^3J=8$ Hz, 3H), 7.56 (d, 3H), 7.80 (br s, 2H), 8.34 (br s, 4H); $^{13}C$ NMR ($CDCl_3$): 24.19, 24.60, 26.10, 31.84, 38.65, 39.87, 40.20, 47.94, 69.77, 74.67, 117.16, 117.76, 119.03, 122.64, 124.33, 126.76, 132.68, 133.06, 146.33, 151.52, 165.81, 176.71; $C_{54}H_{71}N_5O_{10}$·2.5 $CH_2Cl_2$: calc. C, 58.59; H, 6.56; N, 5.99. found C, 58.25; H, 6.35; N, 5.67.

Example 1.2

N, N di-allyl-L-Dopa tris-catecholamide 17 and technetium complex thereof

These compounds have been synthesized according to scheme II:

Scheme II
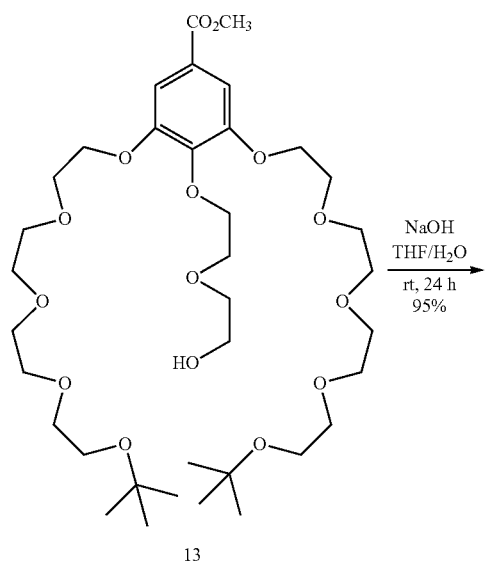
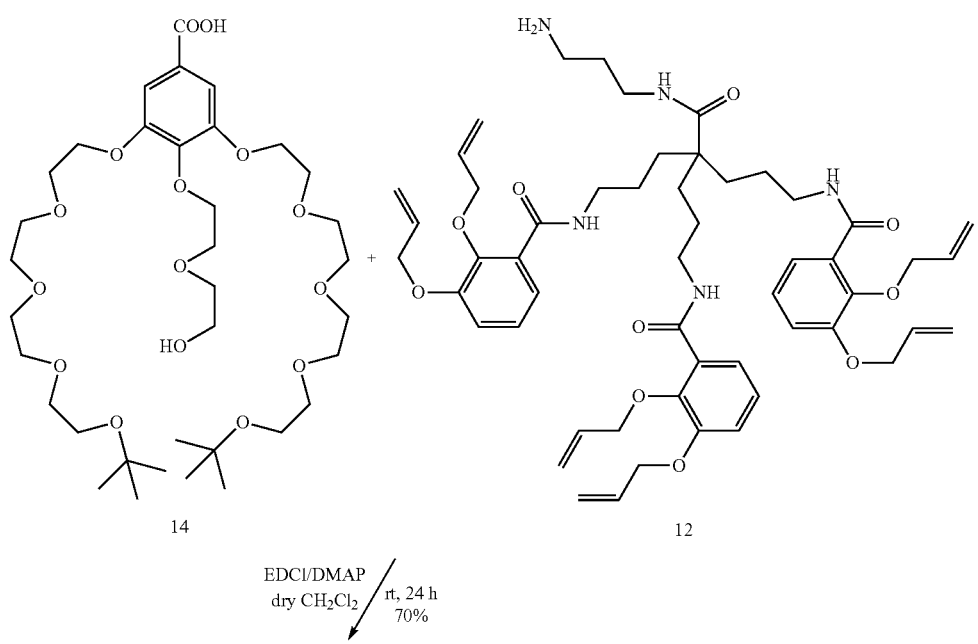

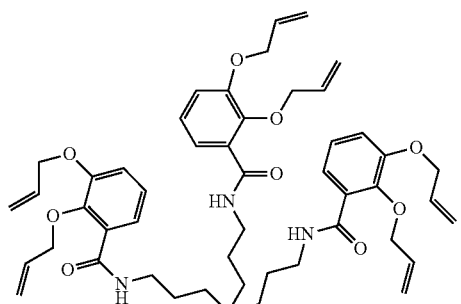

15

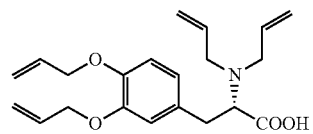

1. EDCl/DMAP
dry CH$_2$Cl$_2$
reflux, 72 h, 50%

2. Pd(PPh$_3$)$_4$ NaBH$_4$
dry THF
rt. 3 h, 81%

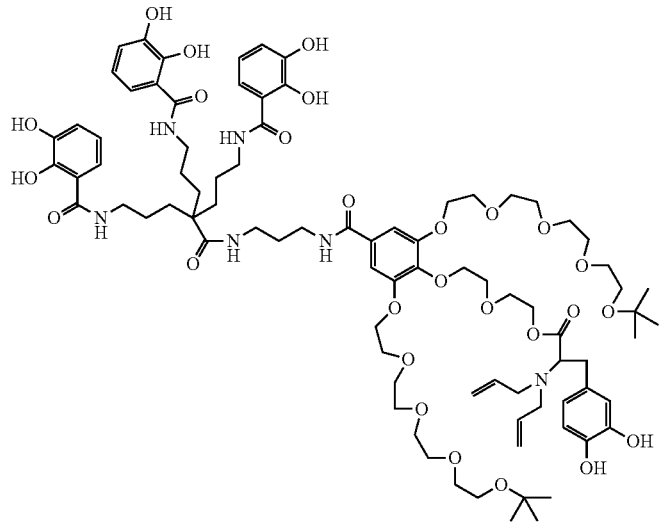

17

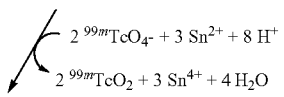

Technetium
Complex

Compound 14:

A solution of sodium hydroxide (0.11 g, 2.82 mmol) in 7.5 mL of water was added to a solution of 13 (1.60 g, 2.17 mmol) in dry THF (30 mL). The reaction mixture was stirred at room temperature for 24 h. After evaporation of THF, the resulting aqueous solution was acidified with concentrated HCl to pH=2 and extracted with CH$_2$Cl$_2$ (2×150 mL). Drying of the combined organic layers over MgSO$_4$ and evaporation of the solvent yielded the desired compound 14 as a yellow oil (1.49 g, 2.06 mmol) with 95% yield and used in next step without further purification. $^1$H NMR (CDCl$_3$): 1.19 (s, 18H), 3.45-3.53 (m, 4H), 3.55-3.70 (m, 24H), 3.72-3.90 (m, 6H), 4.15-4.30 (m, 6H), 7.28 (s, 2H), $^{13}$C NMR (CDCl$_3$): 27.29, 60.95, 61.40, 68.66, 69.46, 70.21, 70.35, 70.42, 70.45, 70.56, 70.95, 72.23, 72.27, 72.93, 109.24, 124.60, 142.43, 152.02, 168.97; C$_{35}$H$_{62}$O$_{15}$: calc. C, 58.15; H, 8.65. found C, 58.20; H, 8.73.

Compound 15:

To a solution of amine 12 (0.58 g, 0.61 mmol) in dry CH$_2$Cl$_2$ (1 00 mL) were added EDCI (0.19 g, 0.98 mmol), DMAP (0.03 g, 0.24 mmol) and then slowly (within 2 h) a solution of carboxylic acid 14 (0.44 g, 0.61 mmol) in dry CH$_2$Cl$_2$ (50 mL). The obtained mixture was stirred for 24 h at room temperature and then was diluted with CH$_2$Cl$_2$ (50 mL). The organic phase was washed with saturated aqueous NH₄Cl solution (2×150 mL) and brine (1×150 mL), dried (MgSO₄), filtered and concentrated in vacuo. Column chromatography (SiO₂, AcOEt) afforded 15 (0.70 g, 0.42 mmol) as colorless oil in 70% yield. H NMR (CDCl₃): 1.17 (s, 18H), 1.40-1.60 (m, 16H), 3.20-3.40 (m, 10H), 3.45-3.52 (m, 4H), 3.53-3.71 (m, 24H), 3.72-3.80 (m, 6H), 4.10-4.20 (m, 6H), 4.51-4.61 (m, 12H), 5.22-5.44 (m, 12H), 5.96-6.10 (m, 7H), 6.96-7.08 (m, 6H), 7.22 (s, 2H), 7.58 (d, $^3J=9$ Hz, 3H), 7.88 (br s, 1H), 8.12 (br s, 3H); 13C NMR (CDCl₃): 24.36, 27.00, 27.20, 27.40, 32.23, 38.20, 38.90, 40.02, 47.95, 53.38, 61.07, 61.55, 68.63, 69.57, 69.78, 70.30, 70.52, 70.53, 70.54, 71.13, 72.30, 72.40, 72.94, 74.65, 106.72, 116.92, 117.76, 118.95, 122.88, 124.29, 127.18, 130.01, 132.75, 133.20, 140.33, 146.30, 151.53, 152.14, 165.26, 166.73, 175.62; MS (MALDI-TOF) m/z: 1677.92 [M+Na]⁺; $C_{89}H_{131}N_5O_{24}$: calc. C, 64.59; H, 7.98; N, 4.23. found C, 65.50; H, 7.75; N, 4.87.

Compound 16:

To a solution of alcohol 15 (0.48 g, 0.29 mmol) in dry CH₂Cl₂ (35 mL) were added EDCI (0.09 g, 0.46 mmol), DMAP (0.015 g, 0.12 mmol) and then the allyl-protected L-DOPA (0.10 g, 0.29 mmol).

The reaction mixture was refluxed for 72 h and then was diluted with CH₂Cl₂ (100 mL). The organic phase was washed with saturated aqueous NH₄Cl solution (2×150 mL) and brine (1×150 mL), dried (MgSO₄), filtered and evaporated to dryness. Column chromatography (SiO₂, CH₂Cl₂/1% MeOH) afforded the compound 16 (0.30 g, 0.15 mmol) as colorless oil in 50% yield. ¹H NMR (CDCl₃): 1.16 (s, 18H), 1.40-1.60 (m, 16H), 2.72-2.80 (m, 1H), 2.92-3.07 (m, 3H), 3.20-3.40 (m, 12H), 3.42-150 (m, 4H), 3.51-3.78 (m, 30H), 4.06-4.15 (m, 6H), 4.21-4.31 (m, 1H), 4.51-4.62 (m, 16H), 5.00-5.13 (m, 4H), 5.20-5.44 (m, 16H), 5.55-5.71 (m, 2H), 5.91-6.11 (m, 9H), 6.64-6.79 (m, 3H), 6.95-7.09 (m, 6H), 7.22 (s, 2H), 7.58 (d, $^3J=9$ Hz, 3H), 7.84 (br s, 1H), 8.12 (br s, 3H); ¹³C NMR (CDCl₃): 24.35, 27.03, 27.22, 27.43, 32.22, 35.38, 39.19, 39.78, 40.00, 47.93, 53.33, 61.06, 63.11, 63.62, 68.63, 68.90, 69.58, 69.76, 69.86, 70.02, 70.32, 70.53, 70.61, 71.12, 72.33, 72.88, 74.63, 106.79, 114.14, 115.60, 116.91, 116.98, 117.28, 117.73, 118.92, 121.89, 122.88, 124.26, 127.18, 130.00, 131.67, 132.74, 133.19, 133.54, 133.65, 136.36, 140.61, 146.29, 146.94, 148.16, 151.51, 152.19, 165.24, 166.73, 172.32, 175.60; MS (MALDI-TOF) m/z: 1995.00 [M+H]⁺, 2016.86 [M+Na]⁺; $C_{110}H_{156}N_6O_{27}$: calc. C, 66.24; H, 7.88; N, 4.21. found C, 65.90; H, 7.78; N, 4.17.

Compound 17:

To a solution of compound 16 (0.057 g, 0.028 mmol) in dry THF (4 mL) was added, under Ar, Pd(PPh₃)₄ (0.005 g, 0.004 mmol). The reaction mixture was stirred for 5 minutes and then NaBH₄ (0.008 g, 0.224 mmol) was added. The resulting suspension was stirred at room temperature, under Ar, for 3 h and then was quenched by MeOH (4 mL) addition. After evaporation of the solvent, the crude was purified by size exclusion chromatography (THF) to yield the compound 17 (0.038 g, 0.023 mmol) as brown solid in 81% yield. H NMR (CD₃OD): 1.21 (s, 18H), 1.45-1.80 (m, 16H), 2.75-2.85 (m, 1H), 2.92-3.03 (m, 1H), 3.13-3.23 (m, 2H), 3.24-3.51 (m, 12H), 3.53-3.90 (m, 34H), 4.18-4.40 (m, 7H), 5.12-5.30 (m, 4H), 5.70-5.91 (m, 2H), 6.35-6.43 (m, 1H), 6.48-6.53 (m, 2H), 6.57-6.74 (m, 6H), 7.18 (d, $^3J=9$ Hz, 3H), 7.38 (s, 2H); ¹³C NMR (CDCl₃): 25.40, 27.78, 28.00, 28.10, 30.11, 33.09, 40.20, 40.65, 40.85, 54.65, 61.98, 63.80, 64.00, 66.10, 69.35, 70.33, 71.05, 71.12, 71.27, 72.13, 73.65, 74.54, 107.10, 108.50, 110.30, 111.68, 114.27, 117.80, 118.06, 118.19, 119.35, 131.80, 137.49, 153.00, 153.20, 153.67, 153.84, 168.88, 170.40, 174.10, 178.80; MS (MALDI-TOF) m/z: 1674.86 [M+H]⁺, 1679.12 [M+5H]⁺; $C_{86}H_{124}N_6O_{27}$: calc. C, 61.71; H, 7.47; N, 5.02. found C, 63.50; H, 8.93; N, 4.11.

Complexation of the compound 17 with technetium:

The compound 17 is dissolved in water (2 mL, 1 mg/mL). A solution (250 microL) of stannous chloride (1 mg/mL, 1.3 mmol) in 0.1 M hydrochloric acid is first added to the above solution and then the 99mTc(VII)O4- solution (220 MBq mL/L). 25 mL of a 1 N aqueous solution of NaOH (25 mmol) and 200 mL of an aqueous solution of sodium ascorbate (150 mM) are also added in order to buffer the reaction mixture at pH 7 and to keep a low redox potential.

The resulting mixture is then stirred at room temperature for 15 min

The radiolabeling process with pertechnetate was efficient and reached 95% $^{99m}$Tc-complexation).

The invention claimed is:

1. Functionalized dendritic nanoprobes of the following formula (I)

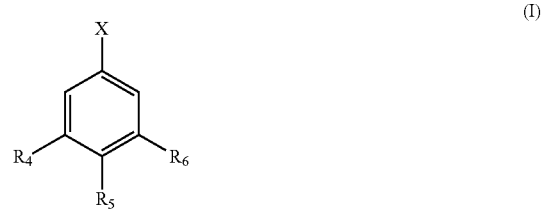

wherein:

for generation 1, $R_4$ and $R_6$ represent independently from each other a chain composed of oligoethyleneglycol patterns, at least one of said oligoethyleneglycol chains being functionalized at its extremity by a group chosen among a fluorophore, or a biocompatible dye, and $R_5$ represents an hydrogen atom or a chain composed of oligoethyleneglycol patterns, said chain being optionally functionalized at its extremity by a group chosen among or a biocompatible dye, for higher generations, $R_5$ represents an hydrogen atom and $R_4$ and $R_6$ represent a dendritic structure (D)m comprising at least one ether of benzyl alcohol, said benzyl being substituted either at positions 3, 4, and 5, or at positions 3 and 5, by chains composed of oligoethyleneglycol patterns, at least one of said oligoethyleneglycol chains being functionalized at its extremity by a group chosen among a fluorophore, or a biocompatible dye, and m=1, 2 or 4, X represents a group of the following formula (II):

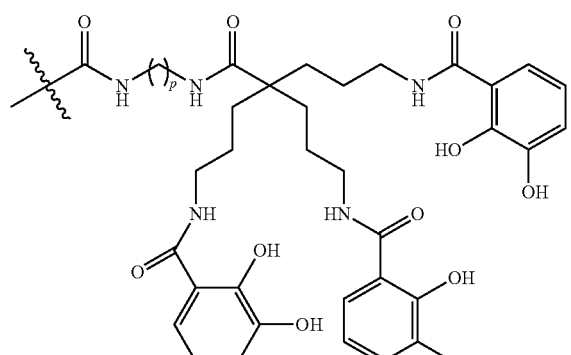

wherein p is from 3 to 6 and wherein the mean diameter of the nanoprobe is from 2 to 60 nm.

2. The nanoprobes according to claim 1, wherein the group of formula (II) is complexed to a ligand or a radio-element to give a group of formula (III):

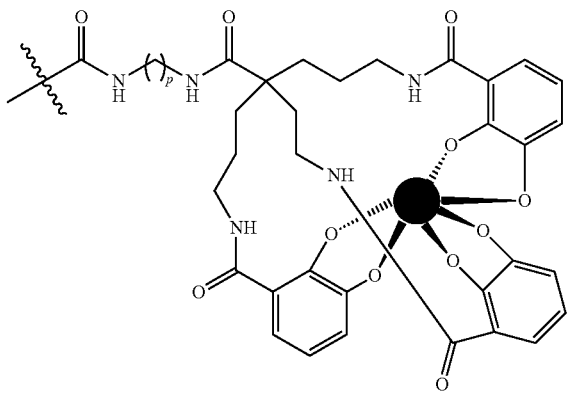

wherein

● represents:

a metallic ion, or a gamma radiation emitter radio-element or a positon emitter radio-element, or an alpha or beta negative radiation emitter radio-element.

3. The nanoprobes according to claim 1, wherein the formula (I) is selected from the following formulae:

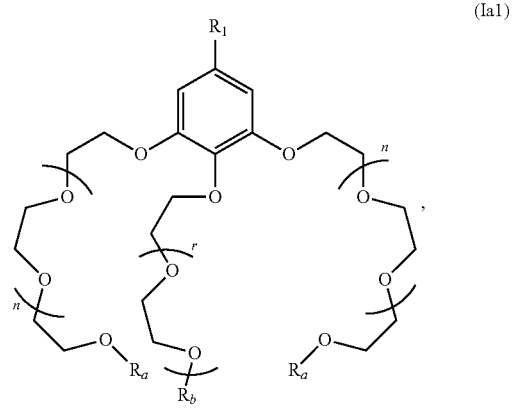

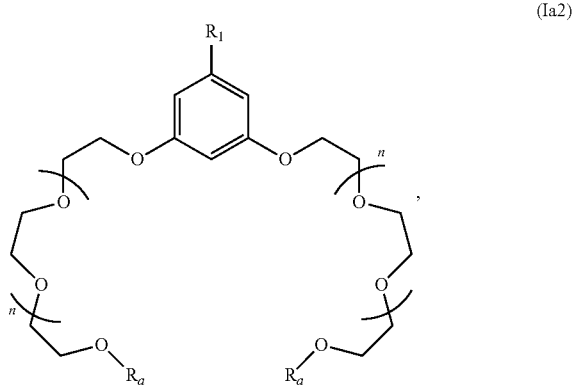

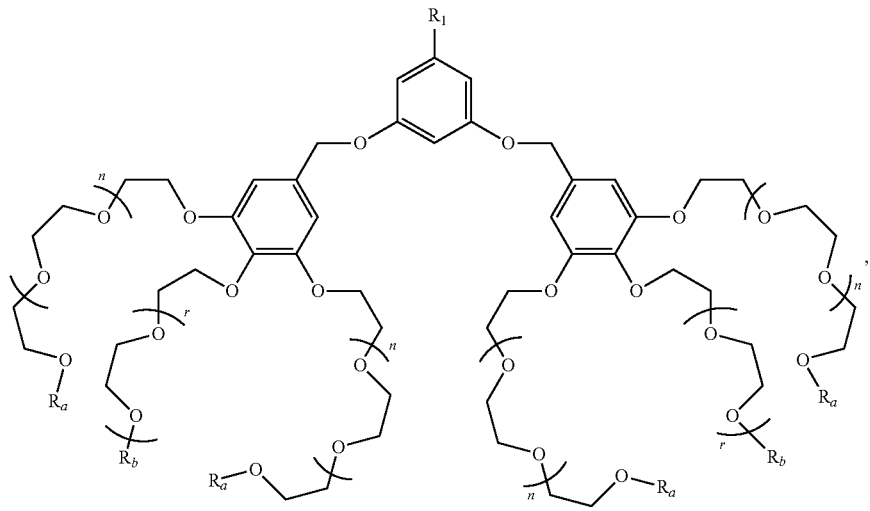
(Ib1)
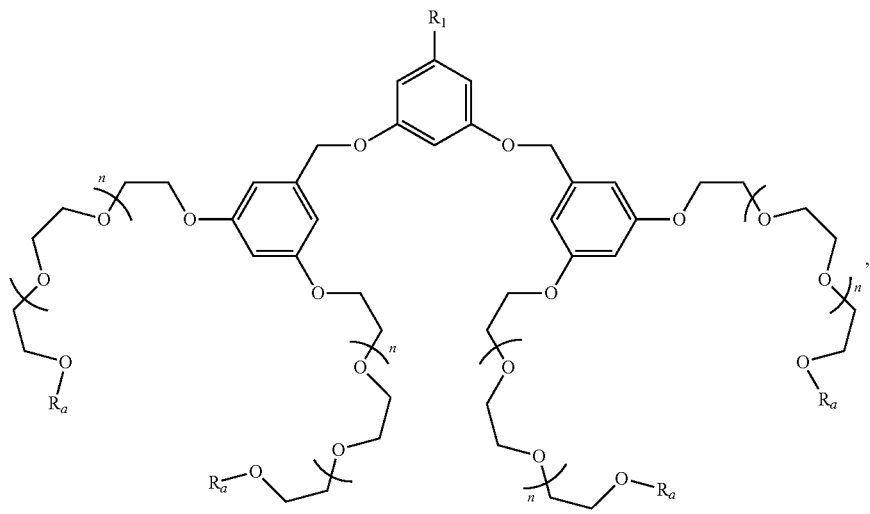
(Ib2)
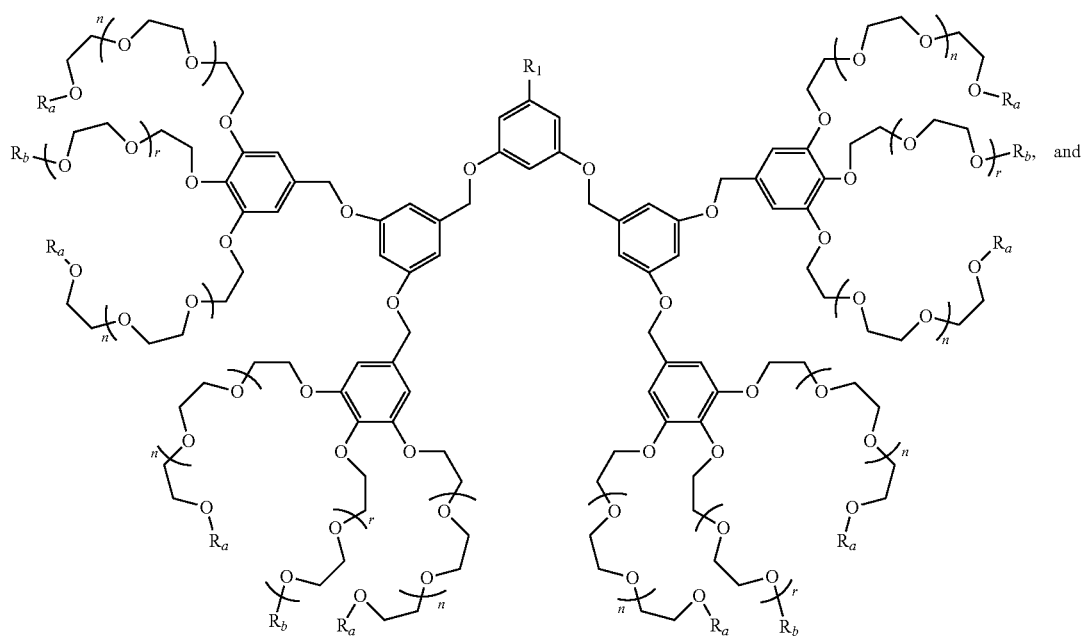
(Ic1) and (Ic2)

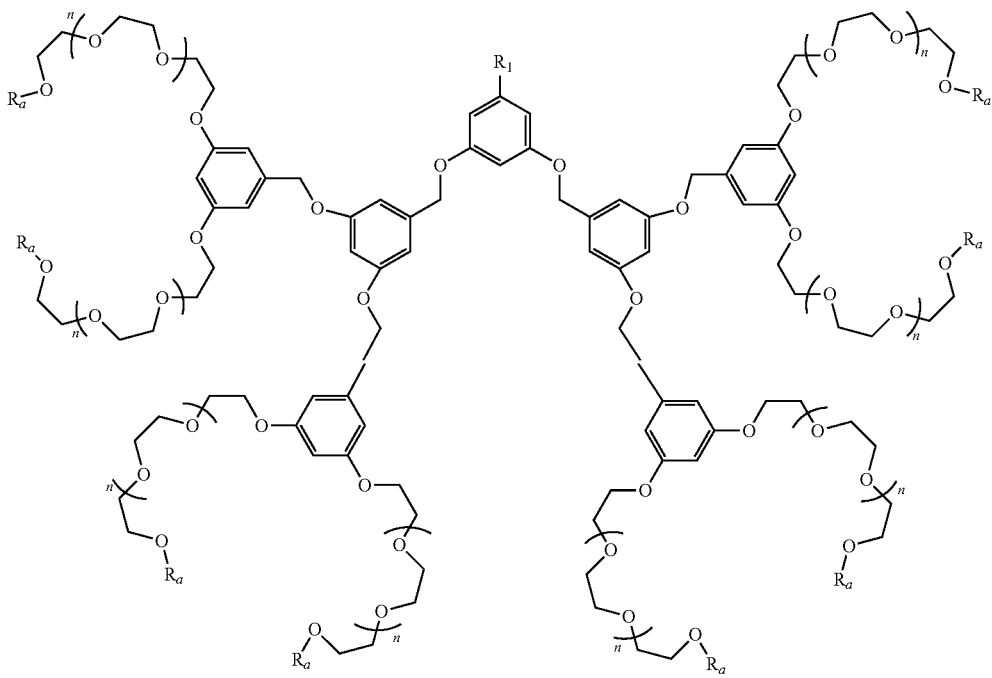

wherein
  R₁ represents the group X of formula (II) as previously defined,
  n is an integer from 1 to 10, r is an integer from 1 to 20, r being ≥n, and
  R$_a$ and R$_b$ independently represents a group selected from:
    a fluorophore, or
    a biocompatible dye bearing at least one group —SO$_3$R$_3$, wherein R$_3$ represents an hydrogen, sodium or calcium atom and eventually one or more groups chosen among —OH and —CO$_2$H, or
    a linear or branched alkyl.

4. The nanoprobes according to claim 3, wherein the structure of formula (I) has the following formulae:

(Ia1a)

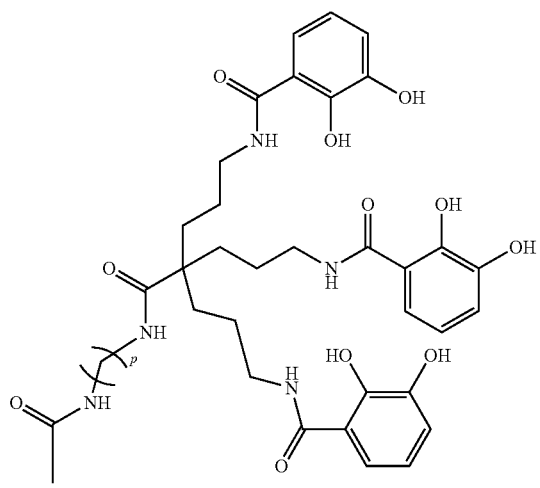

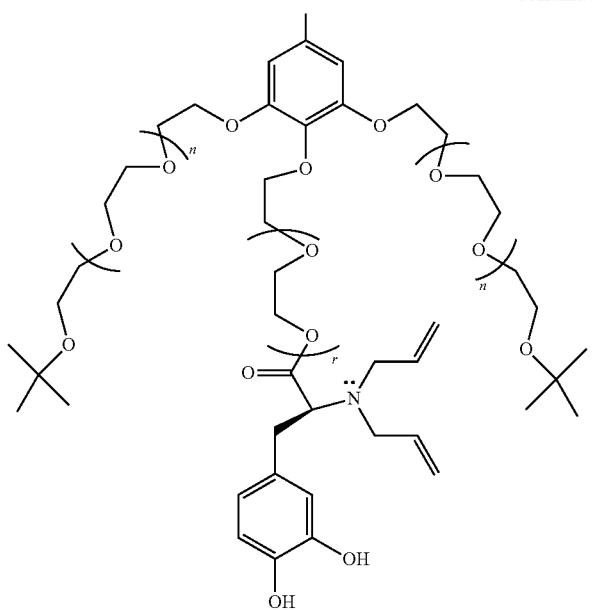
or:
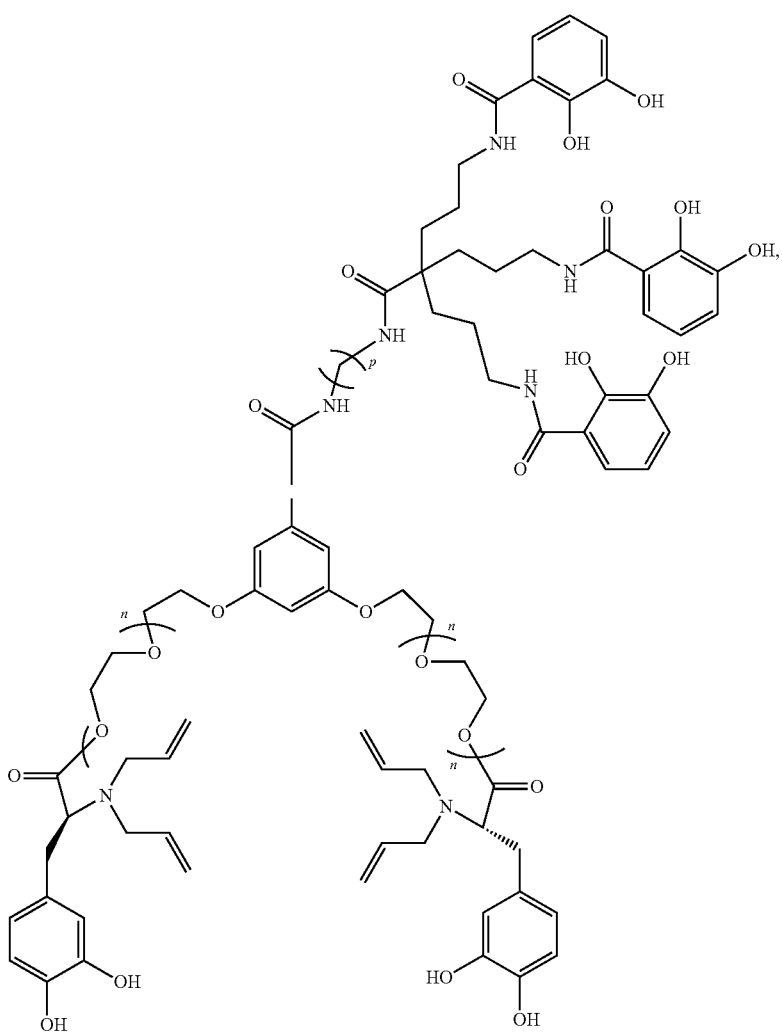
(Ia2a)

or:
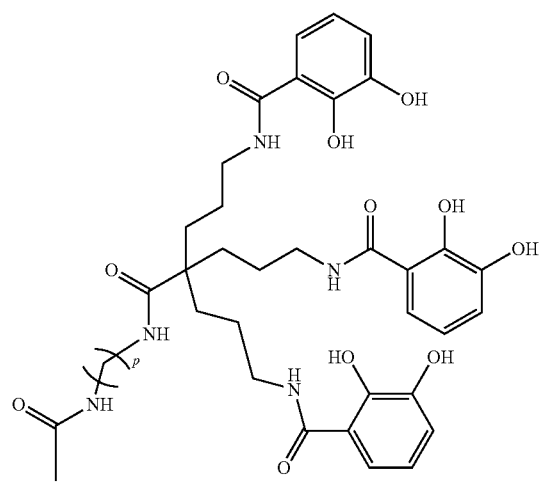
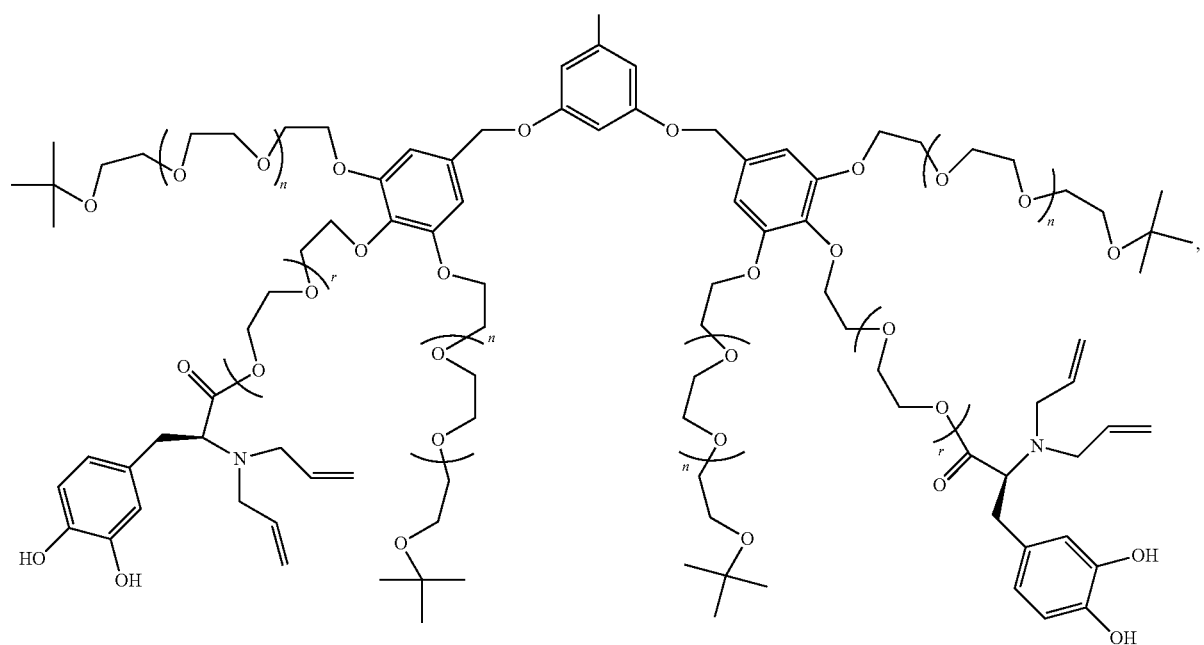

or:

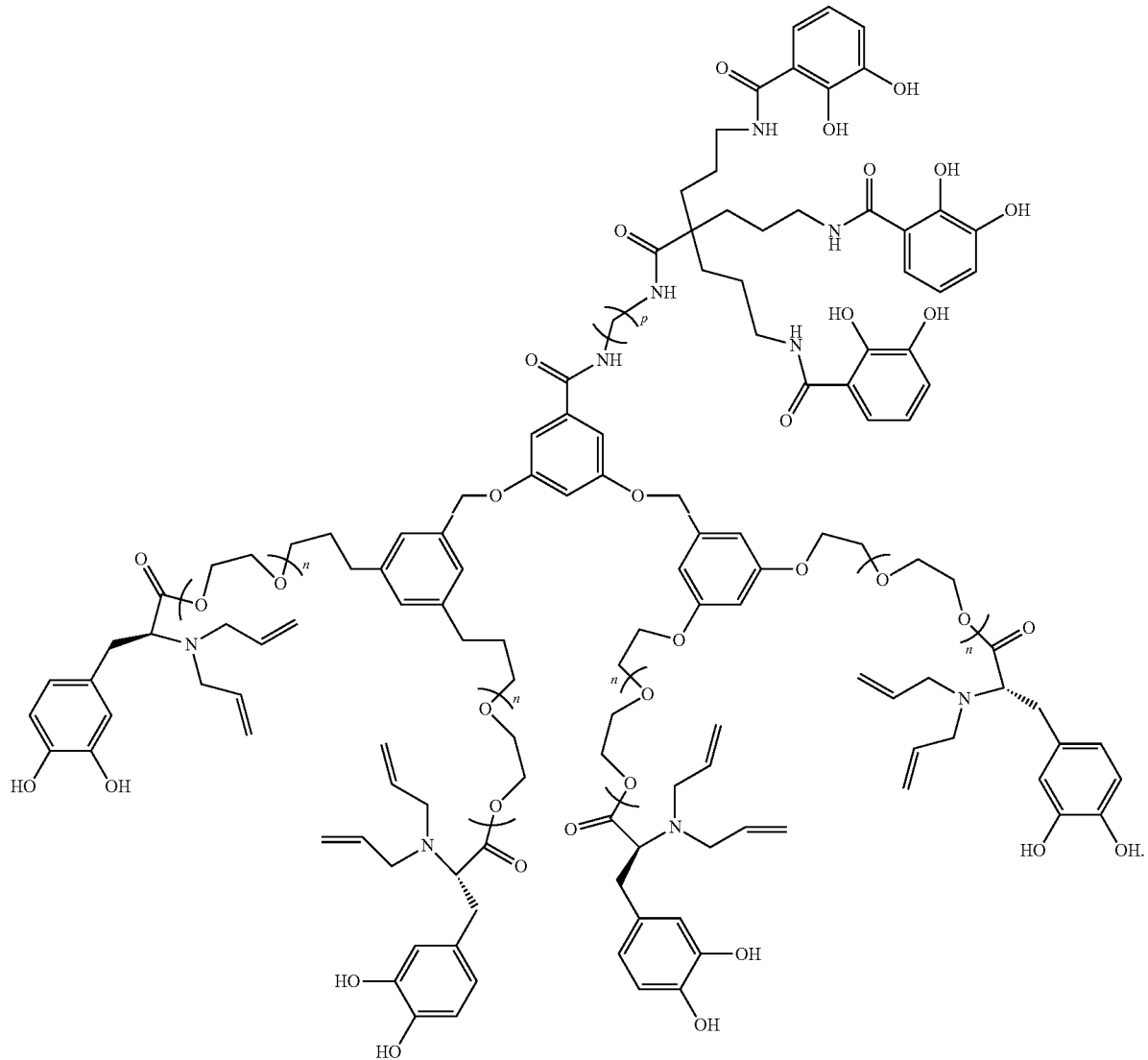

(Ib2)

5. The nanoprobes according to claim 4, further comprising a complexed $^{99m}$technetium.

6. The nanoprobes according to claim 1, in a form suitable for its use as a medicament, or for detecting and/or treating a cancer cell or tissue or organ.

7. The nanoprobes according to claim 6, wherein said cancer is brain cancer.

8. The nanoprobes according to claim 7, wherein said cancer is breast cancer and the organ is the sentinel node.

9. Pharmaceutical or diagnostic compositions comprising the nanoprobes according to claim 1.

10. The nanoprobes according to claim 2, wherein the metallic ion is gadolinium or manganese, and/or the gamma radiation emitter radio-element or positon emitter radio-element is $^{99m}$technetium, $^{64}$copper, $^{(67, 68)}$gallium, or $^{124}$iodine, and/or the alpha or beta negative radiation emitter radioelement is $^{177}$lutetium, $^{90}$yttrium, $^{166}$holmium or $^{186}$rhenium.

11. The nanoprobes according to claim 1, wherein the mean diameter of the nanoprobe is from 15 to 50 nm.

12. The nanoprobes according to claim 1, wherein the mean diameter of the nanoprobe is from 20 to 35 nm.

* * * * *